United States Patent
Landry et al.

(10) Patent No.: US 6,524,312 B2
(45) Date of Patent: *Feb. 25, 2003

(54) INSTRUMENT AND METHOD FOR IMPLANTING AN INTERBODY FUSION DEVICE

(75) Inventors: Michael E. Landry, Austin, TX (US); Erik J. Wagner, Austin, TX (US); Stephen H. Hochschuler, Dallas, TX (US); David J. Krueger, Cedar Park, TX (US)

(73) Assignee: Spinal Concepts, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/755,183

(22) Filed: Jan. 5, 2001

(65) Prior Publication Data

US 2001/0053914 A1 Dec. 20, 2001

Related U.S. Application Data

(63) Continuation-in-part of application No. 09/478,923, filed on Jan. 6, 2000, now Pat. No. 6,447,512.

(51) Int. Cl.[7] .............................................. A61B 17/56
(52) U.S. Cl. ........................ 606/61; 606/80; 623/17.11
(58) Field of Search ............................. 606/60, 61, 62, 606/72, 73, 74, 75, 76, 77, 78, 79; 623/17.11, 17.16

(56) References Cited

U.S. PATENT DOCUMENTS

| | | |
|---|---|---|
| 3,848,601 A | 11/1974 | Ma et al. |
| 4,401,112 A | 8/1983 | Rezaian |
| 4,501,269 A | 2/1985 | Bagby |
| 4,714,469 A | 12/1987 | Kenna |
| 4,743,146 A | 5/1988 | Khmelnitsky et al. |
| 4,743,256 A | 5/1988 | Brantigan |

(List continued on next page.)

FOREIGN PATENT DOCUMENTS

| | | |
|---|---|---|
| DE | 43 23 956 | 10/1994 |
| EP | 0 260 044 | 3/1988 |
| EP | 0 307 241 | 3/1989 |
| EP | 0 880 938 | 12/1998 |
| ES | 9500308 | 2/1995 |
| FR | 2 717 068 | 9/1995 |
| SU | 1424826 | 9/1988 |
| WO | 97/00054 | 1/1997 |
| WO | 97/06753 | 2/1997 |
| WO | 98/17208 | 4/1998 |
| WO | 98/17209 | 4/1998 |
| WO | 98/55052 | 12/1998 |
| WO | WO99/52453 | * 10/1999 |

OTHER PUBLICATIONS

Albee et al., *Bone Graft Surgery in Disease, Injury and Deformity*, D. Appleton–Century Co., Inc., 1940, pp. xi–xv, 1–31, 48–107, and 210–227.

Vich, "Update of the Cloward procedure: new instruments," J. Neurosurg., vol. 81, Nov. 1994, pp. 716–720.

(List continued on next page.)

*Primary Examiner*—Pedro Philogene
(74) *Attorney, Agent, or Firm*—Meyertons, Hood, Kivlin, Kowert & Goetzel, P.C.; Eric B. Meyertons

(57) ABSTRACT

A holder is provided which couples to the spine. In an embodiment, the holder has two conduits into which sleeves may be inserted during a spinal fusion procedure. The holder may have a distractor extending from the bottom of the holder. The distractor secures the holder to the spine and maintains a proper separation distance between adjacent vertebrae. The sides of the distractor may be serrated to better secure the holder to the spine. The sleeves and conduits serve as alignment guides for instruments and implants used during the procedure. In an embodiment, the holder may include holes for fasteners that fixably secure the holder to vertebrae adjacent to a disc space. A flange may be placed around the holder to shield surrounding tissue and to provide a placement location for adjacent blood vessels during the spinal fusion procedure.

114 Claims, 25 Drawing Sheets

U.S. PATENT DOCUMENTS

| | | |
|---|---|---|
| 4,834,757 A | 5/1989 | Brantigan |
| 4,856,503 A | 8/1989 | Schelhas |
| 4,863,476 A | 9/1989 | Sheppard |
| 4,877,020 A | 10/1989 | Vich |
| 4,878,915 A | 11/1989 | Brantigan |
| 4,904,261 A | 2/1990 | Dove et al. |
| 4,936,848 A | 6/1990 | Bagby |
| 4,950,296 A | 8/1990 | McIntyre |
| 4,961,740 A | 10/1990 | Ray et al. |
| 5,015,247 A | 5/1991 | Michelson |
| 5,015,255 A | 5/1991 | Kuslich |
| 5,026,373 A | 6/1991 | Ray et al. |
| 5,055,104 A | 10/1991 | Ray |
| 5,112,354 A | 5/1992 | Sires |
| 5,123,926 A | 6/1992 | Pisharodi |
| 5,147,402 A | 9/1992 | Bohler et al. |
| 5,171,278 A | 12/1992 | Pisharodi |
| 5,192,327 A | 3/1993 | Brantigan |
| 5,263,953 A | 11/1993 | Bagby |
| 5,306,307 A | 4/1994 | Senter et al. |
| 5,306,309 A | 4/1994 | Wagner et al. |
| 5,336,240 A | 8/1994 | Metzler et al. |
| 5,370,697 A | 12/1994 | Baumgartner |
| 5,390,683 A | 2/1995 | Pisharodi |
| 5,397,364 A | 3/1995 | Kozak et al. |
| 5,425,772 A | 6/1995 | Brantigan |
| 5,443,514 A | 8/1995 | Steffee |
| 5,458,638 A | 10/1995 | Kuslich et al. |
| 5,484,437 A | 1/1996 | Michelson |
| 5,489,307 A | 2/1996 | Kuslich et al. |
| 5,489,308 A | 2/1996 | Kuslich et al. |
| 5,505,732 A | 4/1996 | Michelson |
| 5,522,899 A | 6/1996 | Michelson |
| 5,536,271 A | 7/1996 | Daly et al. |
| 5,571,192 A | 11/1996 | Schönhöffer |
| 5,593,409 A | 1/1997 | Michelson |
| 5,601,556 A | 2/1997 | Pisharodi |
| 5,607,424 A | 3/1997 | Tropiano |
| 5,609,635 A | 3/1997 | Michelson |
| 5,609,636 A | 3/1997 | Kohrs et al. |
| 5,632,747 A | 5/1997 | Scarborough et al. |
| 5,645,598 A | 7/1997 | Brosnahan, III |
| 5,653,763 A | 8/1997 | Errico et al. |
| 5,658,337 A | 8/1997 | Kohrs et al. |
| 5,665,122 A | 9/1997 | Kambin |
| 5,669,909 A | 9/1997 | Zdeblick et al. |
| 5,674,295 A | 10/1997 | Ray et al. |
| 5,674,296 A | 10/1997 | Bryan et al. |
| 5,676,701 A | 10/1997 | Yuan et al. |
| 5,683,391 A | 11/1997 | Boyd |
| 5,683,394 A | 11/1997 | Rinner |
| 5,688,279 A | 11/1997 | McNulty et al. |
| 5,693,100 A | 12/1997 | Pisharodi |
| 5,697,977 A | 12/1997 | Pisharodi |
| 5,700,291 A | 12/1997 | Kuslich et al. |
| 5,702,391 A | 12/1997 | Lin |
| 5,702,449 A | 12/1997 | McKay |
| 5,702,450 A | 12/1997 | Bisserie |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar |
| 5,709,683 A | 1/1998 | Bagby |
| 5,713,899 A | 2/1998 | Marnay et al. |
| 5,716,359 A | 2/1998 | Ojima et al. |
| 5,716,415 A | 2/1998 | Steffee |
| 5,716,416 A | 2/1998 | Lin |
| 5,720,746 A | 2/1998 | Soubeiran |
| 5,720,748 A | 2/1998 | Kuslich et al. |
| 5,722,977 A | 3/1998 | Wilhelmy |
| 5,741,253 A | 4/1998 | Michelson |
| 5,749,916 A | 5/1998 | Richelsoph |
| 5,766,253 A | 6/1998 | Brosnahan, III |
| 5,772,661 A | 6/1998 | Michelson |
| 5,776,199 A | 7/1998 | Michelson |
| 5,782,919 A | 7/1998 | Zdeblick et al. |
| 5,785,710 A | 7/1998 | Michelson |
| 5,797,909 A * | 8/1998 | Michelson |
| 5,797,917 A | 8/1998 | Boyd et al. |
| 5,814,084 A | 9/1998 | Grivas et al. |
| 6,080,155 A | 6/2000 | Michelson |
| 6,083,228 A | 7/2000 | Michelson |
| 6,096,038 A | 8/2000 | Michelson |
| 6,113,602 A * | 9/2000 | Sand |

OTHER PUBLICATIONS

Vich, "Anterior cervical interbody fusion with threaded cylindrical bone," J. Neurosurg., vol. 63, Nov. 1985, pp. 750–753.

"Introducing the EndoDowel™," Musculoskeletal Transplant Foundation, Oct. 1996.

Catalog from Musculoskeletal Transplant Foundation, Apr. 1996.

"The MTF EndoDowel™," Musculoskeletal Transplant Foundation, 1996.

"Laparoscopic Bone Dowel Instruments," Sofamor Danek, 1995.

"Laparoscopic Bone Dowel Surgical Technique," Sofamor Danek, 1995.

Brantigan et al, A Carbon Fiber Implant to Aid Interbody Lumbar Fusion (Mechanical Testing, Spine, vol. 16, No. 6 Supplement, 1991.

"Trends in Spine & Disc Surger," MedPro Month, Nov. 1996.

Wittenberg et al., "Compressive Strength of Autologous and Allogenous Bone Grafts for Thoracolumba and Cervical Spine Fusion," Spine, vol. 15, No. 10, 1990, pp. 1073–1078.

"Spinal Fusion Surgery and The BAK™Interbody Fusion System," Spine Tech, Inc., 1993.

"BAK®Cervical Interbody Fusion System," Spine Tech, Inc., 1994.

"The BAK™Interbody Fusion System," Spine Tech, Inc., 1996.

"BAK™Interbody Fusion System (Porosity)," Spine Tech, Inc., 1996.

"BAK™Interbody Fusion System (Biomechanics)," Spine Tech, Inc., 1996.

"BAK™Interbody Fusion System (Instrumentation)," Spine Tech, Inc., 1996.

"Bone Harvester," Spine Tech, Inc., 1996.

"Biomechanical Rationale, The BAK™Interbody Fusion System: An Innovative Solution," Spine Tech, Inc., 1994.

"Surgical Technique using Bone Dowel Instrumentation, for Anterior Approach," Sofamor Danek, 1996.

"Surgical Technique using Bone Dowel Instrumentation, for Posterior Approach," Sofamor Danek, 1996.

Catalog from Cloward®Instruments, 1996.

White et al., *Clinical Biomechanics of the Spine*, J.B. Lippincott Co., 1978, White et al., 1990, pp. 551–552.

Hochschuler et al, "Compressive Strength of Hollow, Allograft Bone Cylinders Proposed for Lumbar Interbody Fusion," NASS 8th Annual Meeting, Oct. 1993.

"MD–I™and MD–II™Custom Machined Cortical Dowels," University of Florida Tissue Bank, 1996.

"MD–III™ Threaded Cortical Dowel, Design Rationale and Surgical Technique," University fo Florida Tissue Bank, 1997.

"Operative Treatment of Degenerative Cervical Disk Disease," Journal of the Southern Orthopaedic Association, 1996.

"Ray Threaded Fusion Cage, Surgical Technique Manual," Surgical Dynamics, 1996.

"Ray Threaded Fusion Cage," Surgicald Dynamics, 1996.

"Surgeons First in Region to Use Lumbar Cage for Spinal Disc Disease," Hohmann Enterprises, 1996.

Heim et al, "The Treatment of Lumbar Degenerative Motion Segment Pain," Spinal Frontiers, Jun. 1997.

"Threaded Bone Dowel," Hohmann Enterprises, 1997.

Technical Monograph, Threaded Cortical Dowel, "Mechanical Characteristics and Evaluation," Universit of Florida Tissue Bank, 1996.

"Tyler Neurosurgeon Jon T. Ledlie, MD, Introduces Bone Dowel Procedures for East Texas–Area Back Pain Sufferers," Tyler Neurosurgical Assoc., 1998.

"Tyler Neurosurgeon Jon T. Ledlie, MD, Introduces Laparoscopic Procedure for East Texas Back Pain Sufferers," Tyler Neurosurgical Assoc., 1998.

"New Approaches to Spine Surgery," USC University Hospital Quarterly, vol. 10, No. 3, 1998.

Beadling, "FDA clears spinal cages for interbody lumbar fusion," Orthopedics Today, vol. 16, No. 10, Oct. 1996, pp. 24–25.

International Search Report, Application No. PCT/US98/08832, mailed Sep. 1, 1998.

International Search Report, PCT/US 01/00451, Jan. 5, 2001.

* cited by examiner

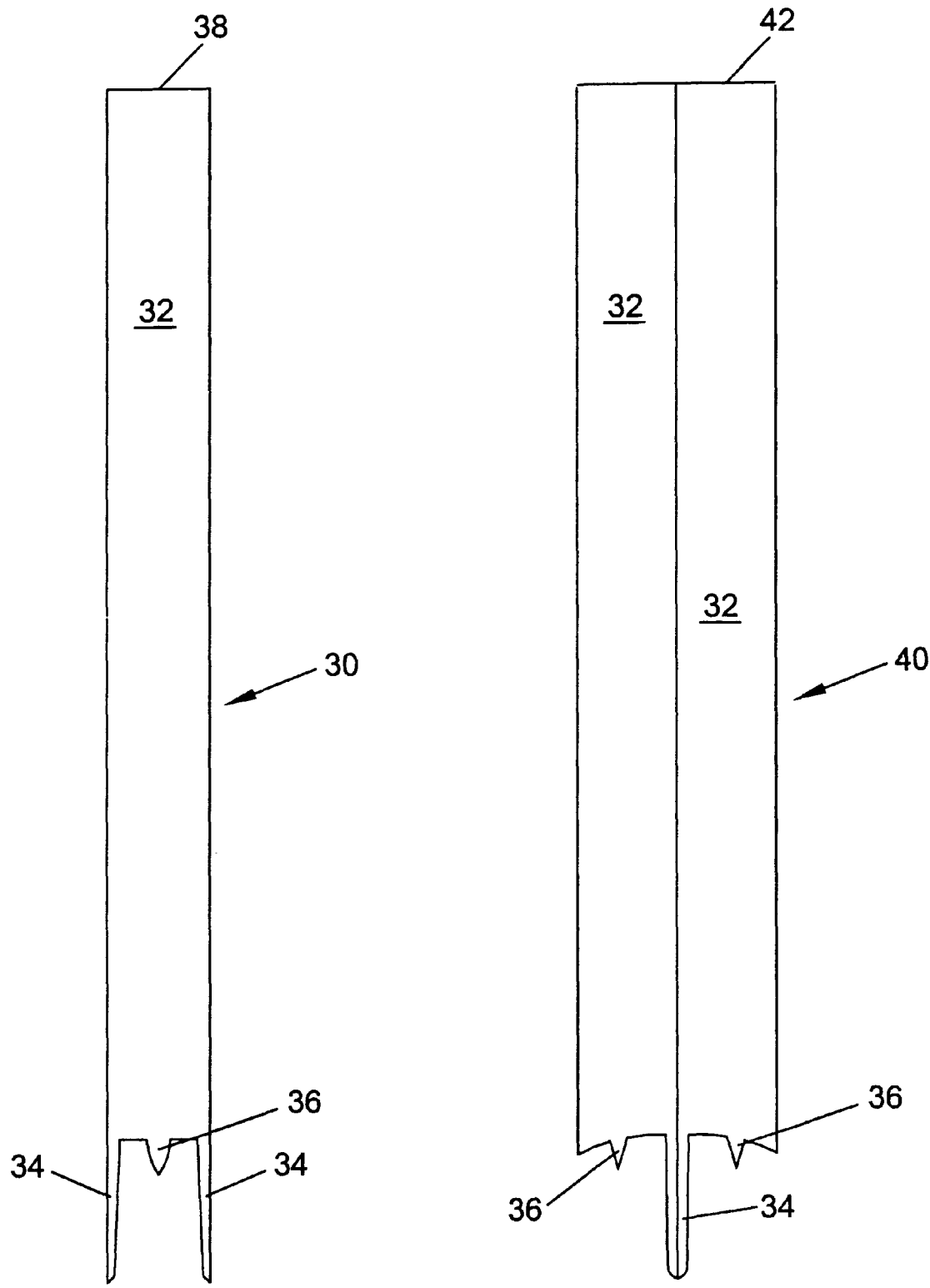

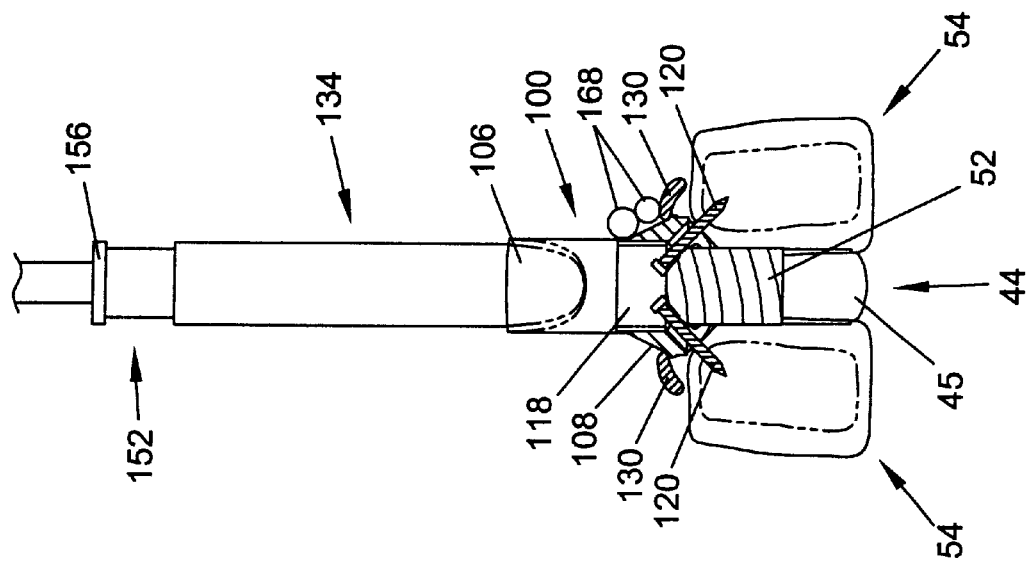
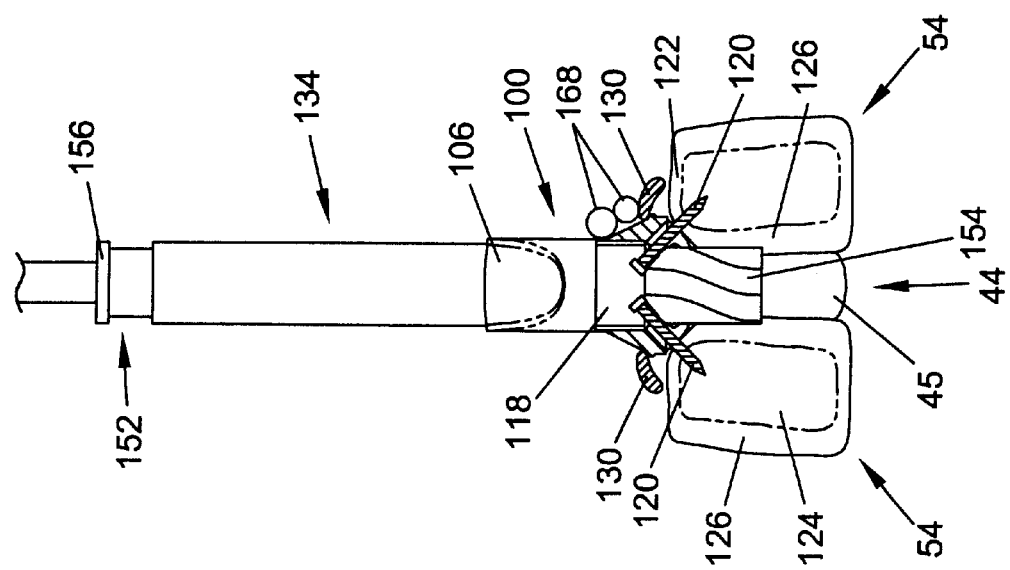

INSTRUMENT AND METHOD FOR IMPLANTING AN INTERBODY FUSION DEVICE

PRIOR APPLICATION

This application is a continuation-in-part of U.S. patent application Ser. No. 09/478,923 filed on Jan. 6, 2000. Now U.S. Pat. No. 6,447,512.

BACKGROUND OF THE INVENTION

1. Field of the Invention

The present invention generally relates to spinal fixation and fusion systems. An embodiment of the present invention relates to an insertion guide used during the insertion of a spinal implant into a disc space between a pair of vertebrae. The implant may be used for correction, fixation, and/or stabilization of a spinal column.

2. Description of the Related Art

An intervertebral disc that becomes degenerated may have to be partially or fully removed from a spinal column. Intervertebral discs may become degenerated due to various causes such as trauma, disease, or aging. Removal or partial removal of an intervertebral disc may destabilize the spinal column. A spinal implant may be inserted into a disc space created by the removal or partial removal of an interverte-bral disc. The spinal implant may maintain the height of the spine and restore stability to the spine. Bone may grow from adjacent vertebrae into the spinal implant. The bone growth may fuse the adjacent vertebrae together.

A spinal implant may be inserted using an anterior, posterior or lateral spinal approach. An anterior spinal approach may require less bone removal and muscle distraction than a posterior spinal approach. Also, an anterior spinal approach may involve less risk of nerve damage than a posterior spinal approach. Intervertebral disc location or other factors may contraindicate an anterior spinal approach.

During an anterior spinal approach, a surgical opening may be made in the abdomen of a patient. The opening may be 25 centimeters (10 inches) or more in depth for some patients. The opening needs to be large enough and deep enough to accommodate instrumentation that inserts a spinal implant within a disc space. A discectomy may be performed to remove portions of a defective or damaged intervertebral disc and create the disc space. The amount of removed disc material may be determined by the size and type of implant that will replace the removed disc material.

The implants may be constructed of any biocompatible materials sufficiently strong to maintain spinal distraction including, but not limited to, bone, metals, ceramics and/or polymers. Implants may be packed with bone graft or a synthetic bone graft substitute to facilitate spinal fusion. Implants may have a variety of shapes, which include, but are not limited to, threaded cylinders, unthreaded cylinders, and parallelepipeds.

A protective sleeve may be used during preparation and insertion of a spinal implant. The protective sleeve may serve to protect abdominal organs, blood vessels and other tissue during a spinal implant procedure using an anterior approach. The sleeve typically extends above the surgical opening during use. The sleeve may maintain distraction of the vertebrae. Also, the sleeve may serve as an alignment guide for tool and implant insertion during the surgical procedure. Protective sleeves may also be used during a spinal fusion procedure using a posterior or lateral approach.

Protective sleeves typically have distractors on a distal end. Distractors are projections that may be inserted into a disc space during a spinal fusion procedure. The distractors may serve to achieve and maintain distraction of adjacent vertebrae. Distractors may also help to secure the protective sleeve to the vertebrae during the procedure. Protective sleeves may have one tube or two parallel tubes. FIG. 1 shows a single-tube protective sleeve, and FIG. 2 shows a dual-tube protective sleeve.

FIG. 1 illustrates a single-tube protective sleeve 30 that may be used in a spinal fusion procedure. A spinal fusion procedure may involve the insertion of one or more implants in a disc space between two vertebrae. Protective sleeve 30 may include a long, hollow tube 32; two distractors 34 on opposite sides of an end of the tube; and two spikes 36 (only one shown) on opposite sides of the end of the tube. Protective sleeve 30 is typically sufficiently long to allow access to a disc space of a large patient during an anterior procedure. Protective sleeve 30 may also be used in a posterior spinal fusion procedure.

A spinal fusion procedure may involve the insertion of two implants in an intervertebral disc space. A discectomy may be performed to provide space for an initial distractor. The initial distractor may be inserted into the disc space. The initial distractor may be rotated to establish an initial separation distance between a pair of vertebrae that are to be fused together. The initial separation distance may be large enough to allow a width of the protective sleeve distractors 34 to fit between the vertebrae. More disc material may be removed adjacent to the initial distractor to accommodate insertion of the protective sleeve distractors 34. A protective sleeve 30 may be placed over the initial distractor. A cap (not shown) may be placed on end 38 of the protective sleeve 30 opposite distractors 34 to protect the end of the sleeve during insertion. Distractors 34 may then be hammered into the disc space by striking the cap with a mallet (not shown). Spikes 36 may be hammered into vertebral bone to stabilize protective sleeve 30 during the implant insertion procedure. Distractors 34 may serve to separate the adjoining vertebrae to a desired separation distance. The cap and initial distractor may be removed from the protective sleeve After insertion of a protective sleeve, a hole may be drilled in the intervertebral disc by inserting a tool with a reaming head attachment through tube 32 and rotating the tool until a predetermined depth is reached. The reaming tool may also remove portions of the end plates of the adjacent vertebrae. In some procedures, the hole is then tapped by inserting a tool with a tap head attachment into tube 32. The tapping tool may be rotated and driven downward until a predetermined depth is reached. After the hole is prepared, an implant may be inserted in the hole by attaching the implant to an implant insertion tool and inserting the implant into the disc space through tube 32. For untapped holes, the implant may be hammered into the hole by striking the implant insertion tool with a mallet. For tapped holes, the implant may be threaded into the hole by rotating the implant insertion tool. The implant insertion tool and the protective sleeve may be removed from the patient.

If a second implant is to be inserted, an initial distractor and cap may be utilized during insertion of the sleeve into the disc space adjacent to the first implant. A hole may be prepared and the second implant may be inserted into the disc space. Alternatively, the protective sleeve 30 may remain inserted in the disc space, and a second single-tube protective sleeve 30 may be inserted adjacent to the protective sleeve. A hole may be prepared and the second implant may be inserted into the disc space through the second sleeve.

The optimal alignment and spacing of implants in a spinal fusion procedure may be determined before surgery. Achieving the predetermined alignment and spacing during surgery may be important to achieve optimal fusing of the adjacent vertebrae. Protective sleeve 30 has characteristics that may make achieving alignment difficult. First, each of the two holes is aligned, reamed, and tapped in a separate procedure. It is often difficult to align and space the holes correctly. Second, the alignment of protective sleeve 30 must be maintained after insertion. Any slight movement of protective sleeve 30, which may act like a lever arm, may result in misalignment of the hole.

FIG. 2 illustrates a dual-tube protective sleeve 40 used in a spinal fusion procedure involving the insertion of two implants into a disc space between a pair of vertebrae. A dual-tube protective sleeve 40 may include long, hollow tubes 32; one or more distractors 34; and one or more spikes 36. Protective sleeve 40 is typically long enough to allow access to an intervertebral disc in a large patient during an anterior procedure. Spinal fusion using implants with protective sleeve 40 may involve the insertion of two implants in a parallel, bilateral position within a disc space.

A discectomy may be performed to provide space for initial distractors. A pair of initial distractors may be inserted into the disc space at desired locations. The initial distractors may be rotated to establish an initial separation distance between the vertebrae. The initial separation distance may allow end of distractor 34 to fit between the vertebrae. More disc material between the initial distractors may be removed to accommodate the distractor 34. A cap (not shown) may be placed on the end 42 of protective sleeve 40 opposite distractor 34. Distractor 34 may be hammered into the disc space by striking the cap with a mallet (not shown). Spikes 36 may be hammered into disc bone on the adjacent vertebrae to help stabilize protective sleeve 40 during the procedure. Distractor 34 may serve to separate the adjoining vertebrae to a desired separation distance.

After coupling the dual-tube protective sleeve to the vertebrae, holes are reamed in the disc space by inserting a tool with a reaming head attachment through tubes 32 and rotating the tool until a predetermined depth is reached. During formation of the holes, a portion of end plates of the vertebrae may be removed so that implants inserted into the holes will contact the vertebrae. In some procedures, the holes are tapped by inserting a tool with a tap head attachment through tubes 32 and rotating the tool until a predetermined depth is reached. After the holes are prepared, implants may be inserted in the holes by attaching the implants to an implant insertion tool and inserting the implants through tubes 32. For untapped holes, the implants may be hammered into the hole by striking the implant insertion tool with a mallet. For tapped holes, the implants may be threaded into the holes by rotating the implant insertion tool. The implant insertion tool is removed. Protective sleeve 40 is also removed.

FIG. 3 shows a representation of implants inserted into disc space 44 using a dual-tube protective sleeve 40. Spinal nerves in the spinal canal 46 are protected by dura 48. Nerves 50 extend from the spinal canal 46. Implants 52 are inserted between two vertebrae 54 (one shown). Care must be taken during insertion of the implants 52 to make sure that the implants do not impinge on the nerves 50.

Like single-tube protective sleeve 30, dual-tube protective sleeve 40 has characteristics that make it difficult to align the implants correctly. First, the alignment of protective sleeve 40 must be maintained after the protective sleeve is coupled to the vertebrae. Any slight movement of sleeve 40, which may act like a lever arm, may result in misalignment of the holes. Second, the long parallel tubes make it difficult to angulate the two implants 52 relative to each other. Angulated implants may be the desired alignment in some spinal fusion procedures. Using a dual-tube protective sleeve 40 has the advantage that the surgical procedure is simplified because there is only one insertion procedure, as opposed to two insertion procedures for a single-tube protective sleeve 30.

Single- and dual-tube protective sleeves share some disadvantages. First, the sleeves are typically unitary members that are long enough to extend out of a 25-centimeter (10 inch) deep surgical opening after being hammered into place. To maintain alignment after insertion, the sleeve must be kept as motionless as possible. The sleeve tends to act like a lever arm, and any slight motion of the sleeve during the procedure may result in misalignment of the implants. The sleeve acting as a lever arm is particularly problematic when the sleeve is handed off during the surgical procedure from one member of the surgical team to another member of the surgical team.

A second disadvantage of protective sleeves is related to the first disadvantage. The sleeve is held in place only by the distractors and the spikes inserted in the disc space. This connection may not be very secure. Because the connection is not secure, the sleeve may have to be held by the members of the surgical team throughout the entire procedure to maintain proper alignment. As noted above, any slight movement can result in the misalignment of the implants.

A third disadvantage of protective sleeves is that they may afford minimal protection to surrounding tissues during a spinal fusion procedure. Major blood vessels, parallel the anterior surface of the spine for much of the spine's lower length. These vessels may be retracted during a spinal fusion procedure. The interface between the distal end of the sleeve and the spinal column is typically not a perfect fit. Gaps may exist between the sleeve and the vertebrae. The presence of gaps creates the risk of drill bits, taps, and implants coming into contact with the blood vessels or other tissue during the procedure. Also, the blood vessels may be pinched between the sleeve and the vertebrae. A nick or cut to a major blood vessel can be life threatening.

Removal of disc material (anulus fibrosus and nucleus pulposus) from the disc space may require special instrumentation. For example, disc material that may be pulled from a disc space with a long rongeur that extends through the sleeve. The length of the rongeur may require that the rongeur be a specially made instrument.

The above-mentioned methods and systems inadequately address the need to angulate implants in some spinal fusion procedures, the need to maintain precise alignment throughout the procedure, and the need to protect surrounding tissues during the procedure. It is therefore desirable that an improved method and system be derived for inserting spinal implants during a spinal fusion procedure.

SUMMARY OF THE INVENTION

A holder or base may allow instruments and spinal implants to be inserted into a disc space during a spinal fusion procedure. The holder may provide a base for a sleeve or sleeves during the spinal fusion procedure. When a sleeve is not being utilized during the procedure, the sleeve may be removed from the holder. The ability to remove the sleeve when the sleeve is not being utilized may prevent the sleeve from being unintentionally used as a lever arm to change the position of a first vertebra relative to a second vertebra during the spinal fusion procedure.

A holder may include a body, one or more sleeve conduits passing through the body from the top to the bottom, and one or more distractors on the bottom of the body. The holder may also include one or more tangs or fastener openings that allow the holder to be affixed to adjacent vertebrae. The body may have a smooth outer surface with no sharp corners or edges. A bottom surface of the holder may be shaped to conform to a shape of an exterior surface of the vertebrae. In some embodiments, the body may be flared near the bottom to provide shielding for surrounding tissue. The flared body may provide the holder with a stable base against vertebrae that are to be fused together.

Sides of a body of a holder may include openings or indentations. The openings or indentations may reduce the weight of the holder. The openings or indentations may also allow an insertion instrument to be easily and strongly coupled to the holder. For a dual sleeve holder, an embodiment of the insertion instrument may be narrow and/or include channels so that the insertion tool may be inserted over initial distractors without the initial distractors contacting the insertion tool. For a single sleeve holder, a sleeve and a cap for the top of the sleeve may be used as the insertion tool. Alternately, a separate insertion tool may be coupled to an opening or indentation of the single sleeve holder to insert the holder between the vertebrae. A separate insertion tool may be used if the sleeve includes a window that could allow the sleeve to bend or deform when the sleeve the holder is impacted into the disc space.

A flange may be placed around a portion of the body of a holder near vertebrae that are to be fused together. The flange may protect tissue and blood vessels from harm during a spinal fusion procedure. Major blood vessels, such as the aorta and the vena cava, may be placed on top of the flange to position the vessels in a known location where the vessels will not be pinched or nicked during the procedure. The flange may inhibit tissue from being pinched, nicked, or otherwise harmed during the spinal fusion procedure. The flange may be made of a rigid or semi-rigid material. A portion of the flange may be made of an elastic material so that the flange may stretch over and slide down the holder. In one embodiment, the holder may include a rim for holding the flange in place after installation. In another embodiment, the holder may include a groove for holding the flange in place. In another embodiment, the flange has an elastic collar, which holds the flange in place against the holder.

A sleeve may be placed within a sleeve conduit of a holder during a spinal fusion procedure. Instrumentation may be inserted through the sleeve to prepare the disc space for an implant. The instrumentation may include, but is not limited to drills, taps and tissue removers. The implant may be inserted into a prepared disc space through the sleeve. In some holder embodiments, an inner surface of a sleeve conduit may include a shoulder to limit the insertion distance of a sleeve into the conduit. Above a shoulder, a conduit may be sized to match the outer diameter of a protective sleeve. Below the shoulder, the conduit may be sized to match the outer diameter of instrument heads and implants to be used in the procedure. In some embodiments, the shoulder may include slots configured to engage distractors on protective sleeves. The slots may allow the holder to be used with single-tube protective sleeves that include distractors.

Embodiments of a holder may have non-circular conduits. The cross sectional shape of the holder conduits and the protective sleeves inserted into the holder may be any desired shape that allows for the insertion of spinal implants into a disc space. For example, the cross sectional shape of the conduits may be rectangular if the cross sectional shape of the spinal implants are generally rectangular. Other embodiments of the holder may have overlapping circular conduits or conduits which do not have a regular geometric shape. Embodiments of holders that have circular conduits may be constructed with conduits of different diameters to accommodate protective sleeves and implants of different diameters.

Embodiments of holders may be provided with non-parallel angled conduits. Non-parallel conduits allow the insertion of implants at oblique angles to improve spinal fusion and to protect nerves posterior to the disc space. Other holder embodiments may have parallel conduits.

In an embodiment of a holder, a distractor or distractors of the holder are driven into an intervertebral disc space. In an embodiment of a dual sleeve holder, the holder has a central distractor between sleeve conduits of the holder. In an embodiment of a dual sleeve holder, the holder includes a pair of lateral distractors located near opposite ends of the sleeve conduits. In an embodiment of a dual sleeve holder, the holder includes a central distractor, and a pair of lateral distractors located near opposite ends of the sleeve conduits. In an embodiment of a single sleeve holder, the holder may include a pair of distractors located near opposite ends of a sleeve conduit. A distractor of a holder may establish a separation distance between adjacent vertebrae. A distractor may secure the holder to the vertebrae.

Distractors may include a wedge-shaped portion to facilitate distraction of a pair of adjacent vertebrae. Distractors may include curved guide surfaces that guide an implant or instruments to desired positions within a disc space. A portion of an outer surface of a distractor may include serrations or surface roughening. The serrations or surface roughening may help to secure the holder to adjacent vertebrae during a spinal fusion procedure. A distractor or distractors of a holder may be tapered. The distraction provided by the holder may allow a separation distance between the vertebrae to be greater near anterior surfaces of the vertebrae. The tapered distractor or distractors may allow insertion of an implant or implants that provide lordotic adjustment.

A holder may be affixed to a pair of vertebrae during a spinal fusion procedure. In an embodiment of a holder, a tang is driven into a vertebra to affix the holder to the vertebrae. The tang may include serrations or surface roughening that securely couples the holder to the vertebra. In an embodiment a tang is driven into each vertebra of a pair of vertebrae. In alternate embodiments, holders may include fastener openings. Fasteners may be driven into a vertebra or into the vertebrae through the fastener openings to fasten the holder to the vertebrae. The fasteners may be, but are not limited to, screws, nails, rivets, trocars, pins, and barbs.

Protective sleeves may be inserted into, and may be removed from, conduits in a holder. A portion of the sleeve may have a window or slot located adjacent to the top of the holder. The window may serve as a view-port to provide increased visibility near the procedure site. A keyway in the sleeve may be placed over a pin in a body of the holder during insertion of the sleeve into the holder. When the pin engages the keyway, the sleeve may be rotated to secure the sleeve within holder. The pin and keyway may ensure that the window is positioned in a desired location. In embodiments of sleeves and dual sleeve holders, the desired location of the window is adjacent to a second conduit in the holder after the sleeve is inserted and rotated in a first conduit of the holder. The position of the window may inhibit tissue or blood vessels from being damaged by instruments inserted within the sleeve.

In some embodiments, the inner surfaces of the conduits may contain shoulders to limit the insertion distance of protective sleeves in the conduits. Above a shoulder, a conduit may be sized to match the outer diameter of a protective sleeve. Below the shoulder, the conduit may be sized to match the outer diameter of instrument heads and implants to be used in the procedure. In some embodiments, the shoulder may include slots configured to engage distractors on protective sleeves; thus allowing the holder to be used with single-tube protective sleeves having distractors.

The height of a holder, when inserted in a disc space between two vertebrae, may be substantially less than a length of a protective sleeve. During a spinal fusion procedure, a protective sleeve may be inserted into a sleeve conduit of the holder when needed and removed when not needed without affecting alignment of the holder relative to the vertebrae. Removal of a protective sleeve from the holder may decrease the likelihood of a protective sleeve being inadvertently used as a lever arm during the procedure. Removing a protective sleeve from the holder may increase visibility at the procedure site. Removing a protective sleeve may also allow for easy access to the disc space to irrigate or aspirate the surgical site.

An advantage of a holder is that the holder may be securely coupled to vertebrae by a fastener and/or tangs. Securely coupling the holder to the vertebrae may maintain alignment and position of the holder throughout an implant insertion procedure. The holder may have a low profile. The low profile may inhibit the holder from being unintentionally contacted and moved during an implant insertion procedure. Further advantages of a holder may include that the holder is sturdy, durable, light weight, safe, simple, efficient, and reliable; yet the holder may also be easy to manufacture and use.

Another advantage of a holder is that a body of the holder may include a pin that engages a keyway of a sleeve positioned within a sleeve conduit. The pin and keyway may allow a window in the sleeve to be positioned at a desired location relative to the holder. The position of the window may provide increased visibility during the spinal fusion procedure. The position of the window may inhibit tissue from entering the window and contacting a portion of an instrument within the sleeve. The window may be positioned at a desired position by rotating the sleeve. In an embodiment, rotating the sleeve approximately 45° after insertion into the sleeve conduit positions the window in the desired location. Material may be removed from the disc space through the opening without requiring removal of the sleeve from the holder or removing the material through the entire length of the sleeve.

BRIEF DESCRIPTION OF THE DRAWINGS

Further advantages of the present invention will become apparent to those skilled in the art with the benefit of the following detailed description of embodiments and upon reference to the accompanying drawings in which:

FIG. 1 illustrates a single-tube protective sleeve;

FIG. 2 illustrates a dual-tube protective sleeve;

FIGS. 19a–19e illustrate steps included in a spinal fusion procedure using an embodiment of a holder;

DESCRIPTION OF EMBODIMENTS

Figure 3:
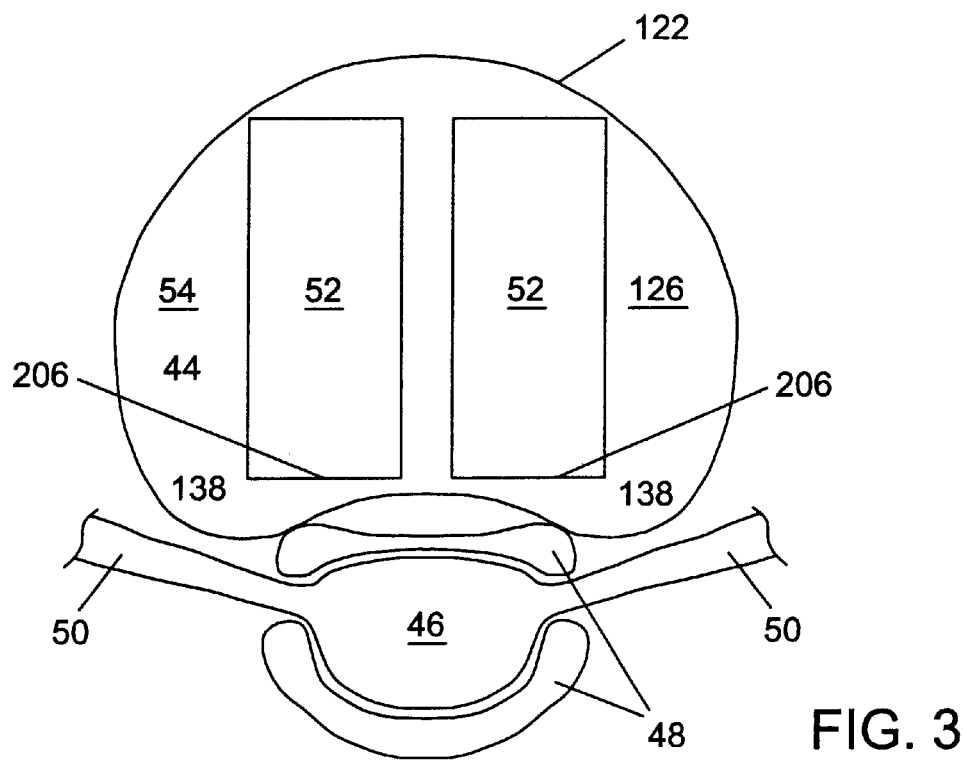
FIG. 3 is a representation of implants inserted in parallel within a disc space by a dual-tube protective sleeve or by an embodiment of a holder that has parallel conduits.
Figure 4:
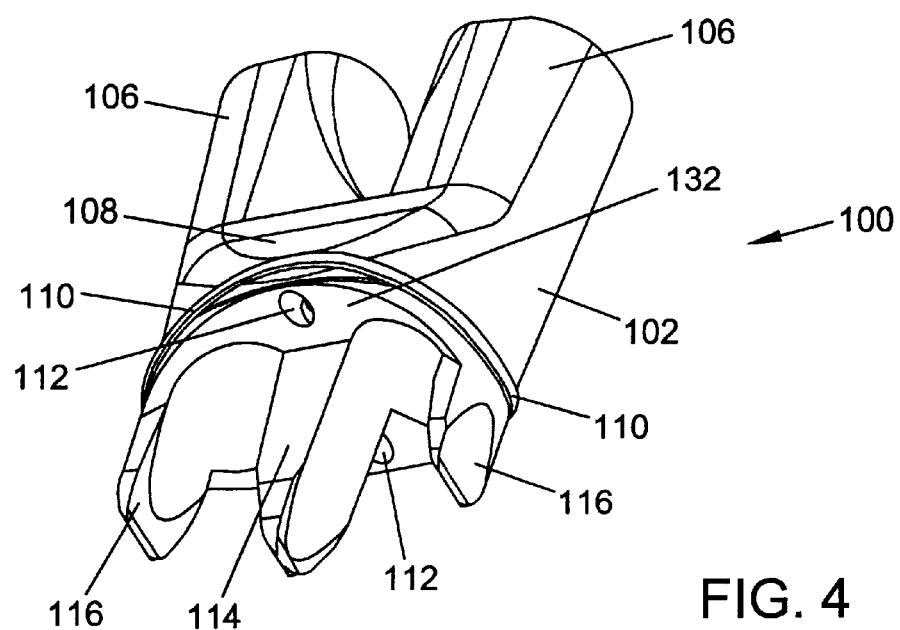
FIG. 4 is a perspective view of an embodiment of a holder.

Referring to the drawings, and particularly to FIG. 4, a holder or base that may be used as an implant insertion guide during a spinal fusion procedure is designated generally as 100. A holder may be used to support a sleeve during a spinal fusion procedure. A base may be used with or without a sleeve during a spinal fusion procedure. For illustrative purposes only, the following description will describe a holder. A person having ordinary skill in the art will understand that a holder may be used as a base, and a base may be used as a holder. A sleeve may be advantageously used during an implant insertion procedure. A top surface of the sleeve may be a stop for an instrument that limits an insertion depth of the instrument into a disc space.

FIGS. 4–10 show views of embodiments of holders 100. A holder 100 may include body 102, conduits 104 through the body, conduit extenders 106, flared portion 108, flange rim 110, fastener holes 112 distractor 114, and lateral distractors 116. In an embodiment of a holder 100, a height from a top of a conduit extender 106 to a lowest portion of the body 102 may be less than about 15-centimeters (six inches). In alternate embodiments of holders, heights of holders from tops of a conduit extenders 106 to the lowest portions of the bodies 102 may be less than about 10-centimeters (four inches), or the heights may be less than about 5-centimeters (2 inches).

Conduits 104 (depicted in FIG. 7) of a holder 100 may have circular cross sections. Alternatively, the conduits 104 may have any desired cross sectional shape, such as rectangular or ellipsoidal, to correspond to instruments and implants used during a spinal fusion procedure.

Figure 8:
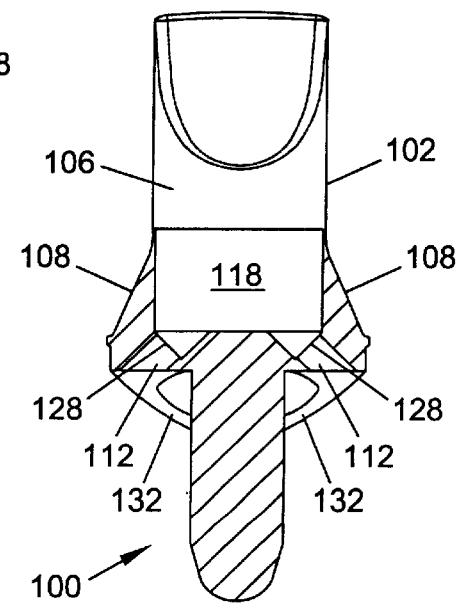
FIG. 8 is a cross-sectional view of an embodiment of a holder taken substantially along line 8—8 of FIG. 5.

As depicted in FIG. 8, the body 102 of a holder 100 may have flared portion 108. The flared portion 108 may allow for angulation of fastener holes 112. Fastener holes 112 may be located in slot 118. Angulated fastener holes 112 allow fasteners 120 inserted through the fastener holes to penetrate adjacent vertebrae 54 through end caps 122 of the vertebrae and into cancellous bone 124, as shown in FIG. 28d. Attaching the holder 100 to the vertebrae 54 with fasteners 120 placed through end caps 122 may minimize weakening of the end plates 126 of the vertebrae. Shoulders 128 may limit an insertion depth of the fasteners 120 into the holder 100. Fasteners 120 may be any type of fastening device including, but not limited to, screws, nails, rivets, trocars, pins, and barbs.

Figure 12:
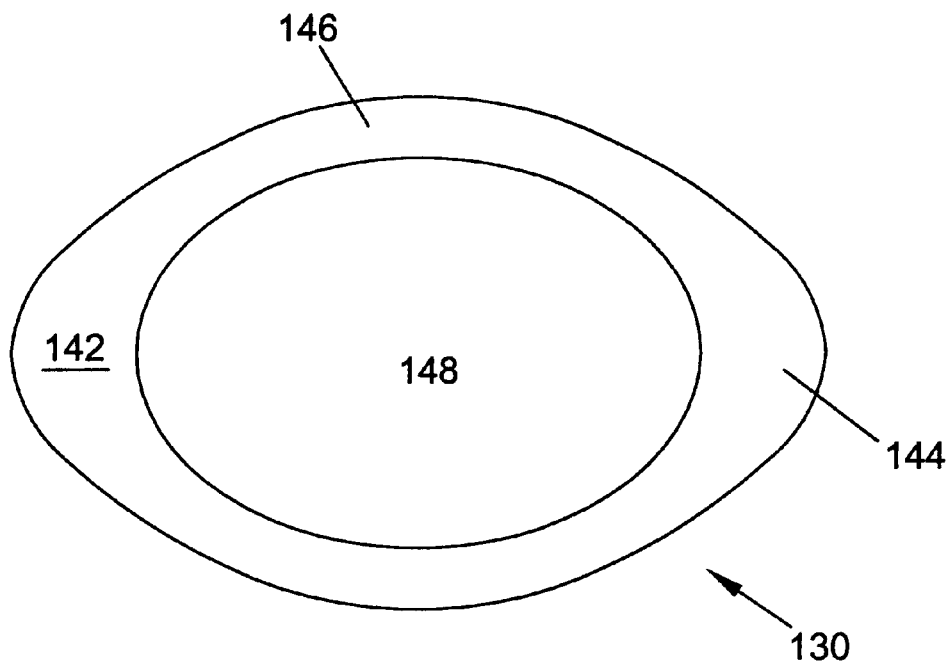
FIG. 12 is a top view of an embodiment of a holder flange.
Figure 13:
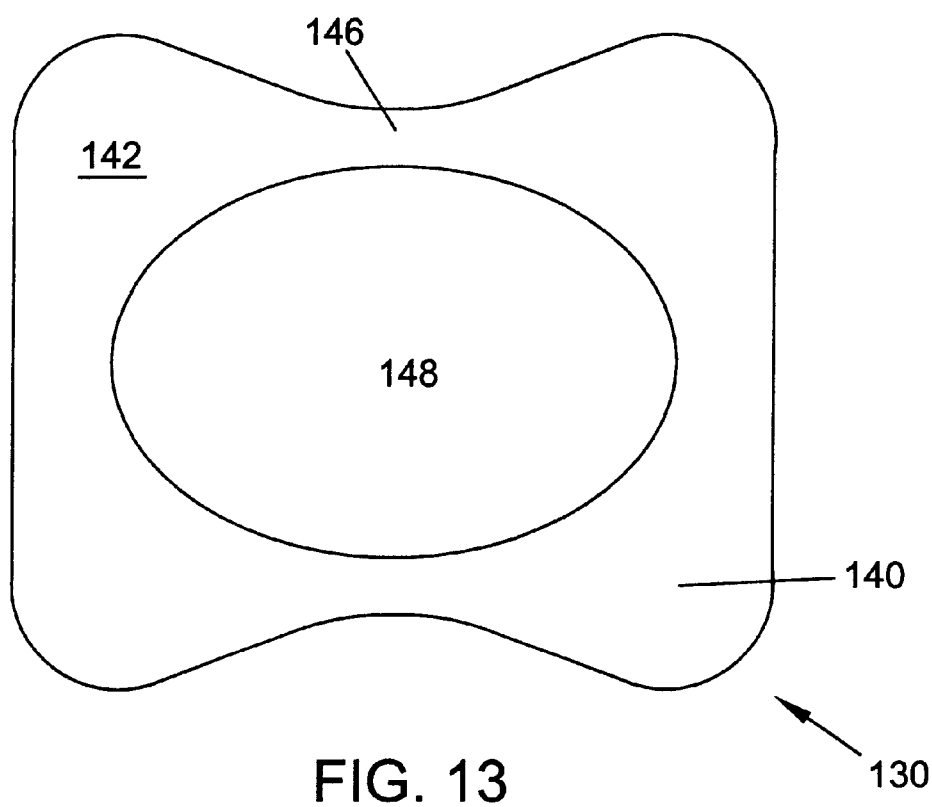
FIG. 13 is a top view of an embodiment of a holder flange.

A flared portion 108 of a body 102 of a holder 100 may shield blood vessels, nerves, and other soft tissue from damage by the body and tools used during a spinal fusion procedure. In addition, the flared portion 108 may increase the circumference of holder 100 to a maximum near flange rim 110. An optional flange 130 (depicted, for example, in FIG. 12) may slip over the top of a holder 100 and reside against the rim 110.

Figure 5:
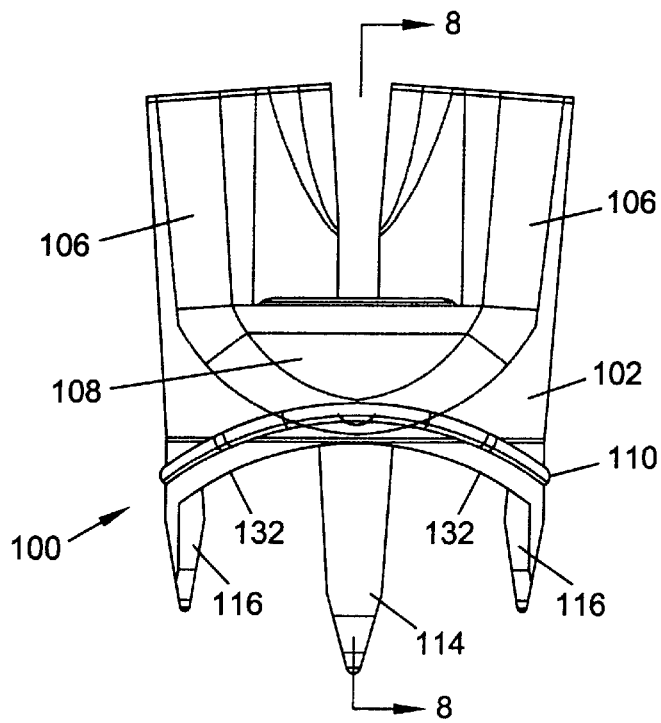
FIG. 5 is a front view of an embodiment of a holder.
Figure 6:
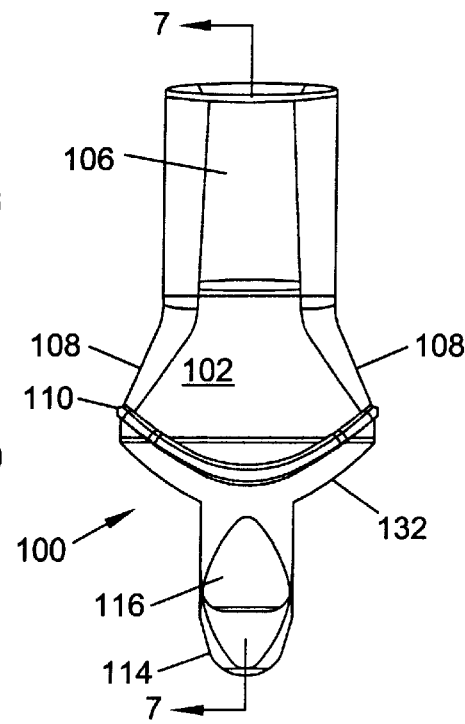
FIG. 6 is a side view of an embodiment of a holder.

The flared portion 108 of the holder 100 may provide a stable base that extends over a portion of adjacent vertebrae when the holder is inserted into a disc space. A shape of bottom 132 of the holder 100 may be curved as depicted in FIG. 5. When the holder 100 is coupled to a pair of vertebrae, the shape of the bottom 132 may allow edges of the holder to closely conform to surfaces of end caps 122 of the vertebrae 54 (depicted in FIG. 28d). Close conformance between the edges of holder 100 and end cap surfaces of adjacent vertebrae 54 may inhibit pinching of tissue or blood vessels between the holder 100 and the vertebrae during an implant insertion procedure.

Figure 7:
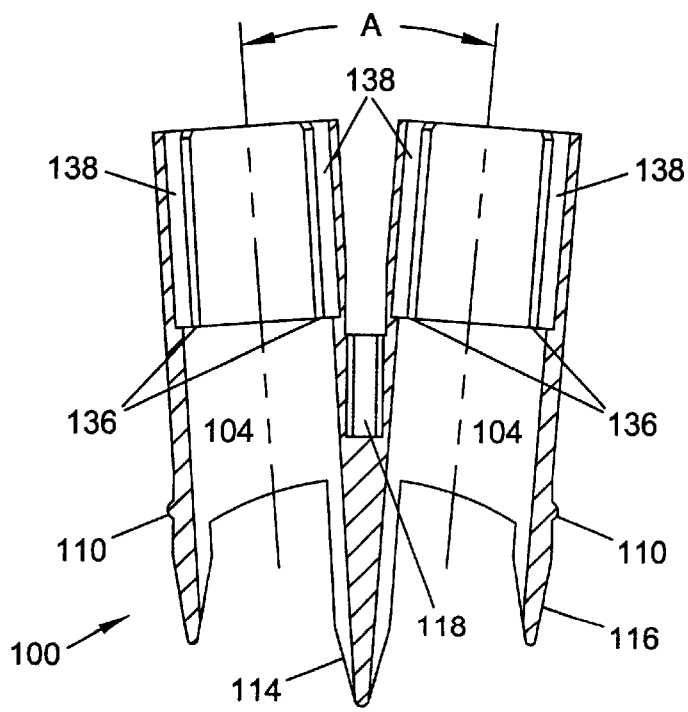
FIG. 7 is a cross-sectional view of an embodiment of a holder taken substantially along line 7—7 of FIG. 6.
Figure 9:
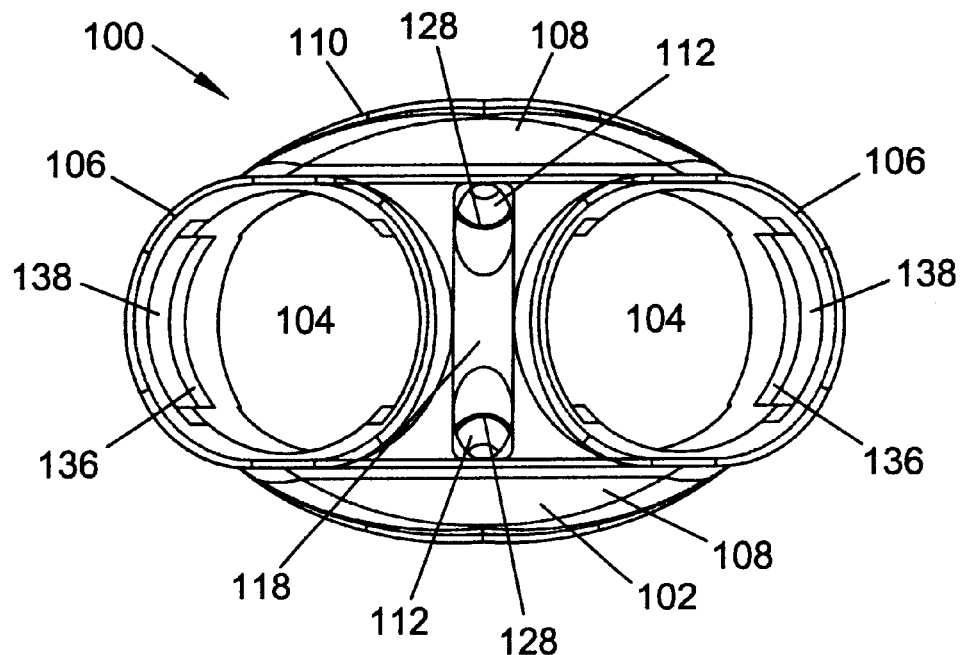
FIG. 9 is a top view of an embodiment of a holder.
Figure 10:
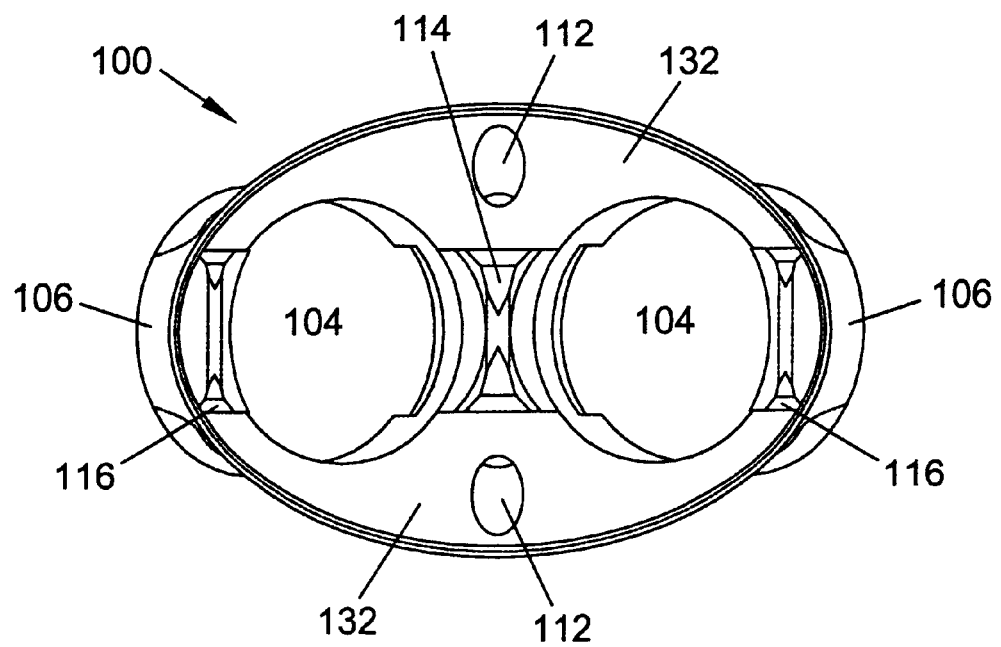
FIG. 10 is a bottom view of an embodiment of a holder.

A perimeter of a conduit 104 at a top end of a holder 100 may closely conform to an outer perimeter of a protective sleeve 134 (depicted, for example, in FIG. 16) inserted into the conduit. Each conduit 104 of a holder 100 may include a shoulder 136, as depicted in FIG. 7. A holder 100 may have one, two or more conduits. A shoulder 136 may limit an insertion depth of a protective sleeve 134 into a conduit 104. As shown in FIG. 9 and in cross section in FIG. 7, a conduit 104 may include slots 138. Slots 138 may allow a holder 100 to be used with a single-tube protective sleeve 30 having distractors 34, such as the sleeve illustrated in FIG. 1. The distractors 34 may fit within the slots 138. In other embodiments, conduits 104 may be configured to receive protective sleeves that do not include distractors. The shoulders 136 may extend fully around the conduits 104.

Distractors 114 and lateral distractors 116 of a holder 100 may be protrusions that extend from bottom 132 of the holder body 102. Distractor 114 may serve to maintain distraction of adjacent vertebrae during a spinal fusion procedure. The distractor 114 may establish a separation distance between the vertebrae during the procedure. Lateral distractors 116 may also serve to maintain distraction. The lateral distractors 116 may inhibit rotation of the holder 100 during the procedure. The lateral distractors 116 may also maintain a parallel orientation of the vertebrae during the procedure. Distractor 114 and lateral distractors 116 may be substantially wedge-shaped to facilitate insertion into a disc space. Surfaces of distractor 114 and lateral distractors 116 may be curved to match the curvature of the conduits 104 so that the distractors serve as partially enclosed extensions of the conduits.

Figure 11:
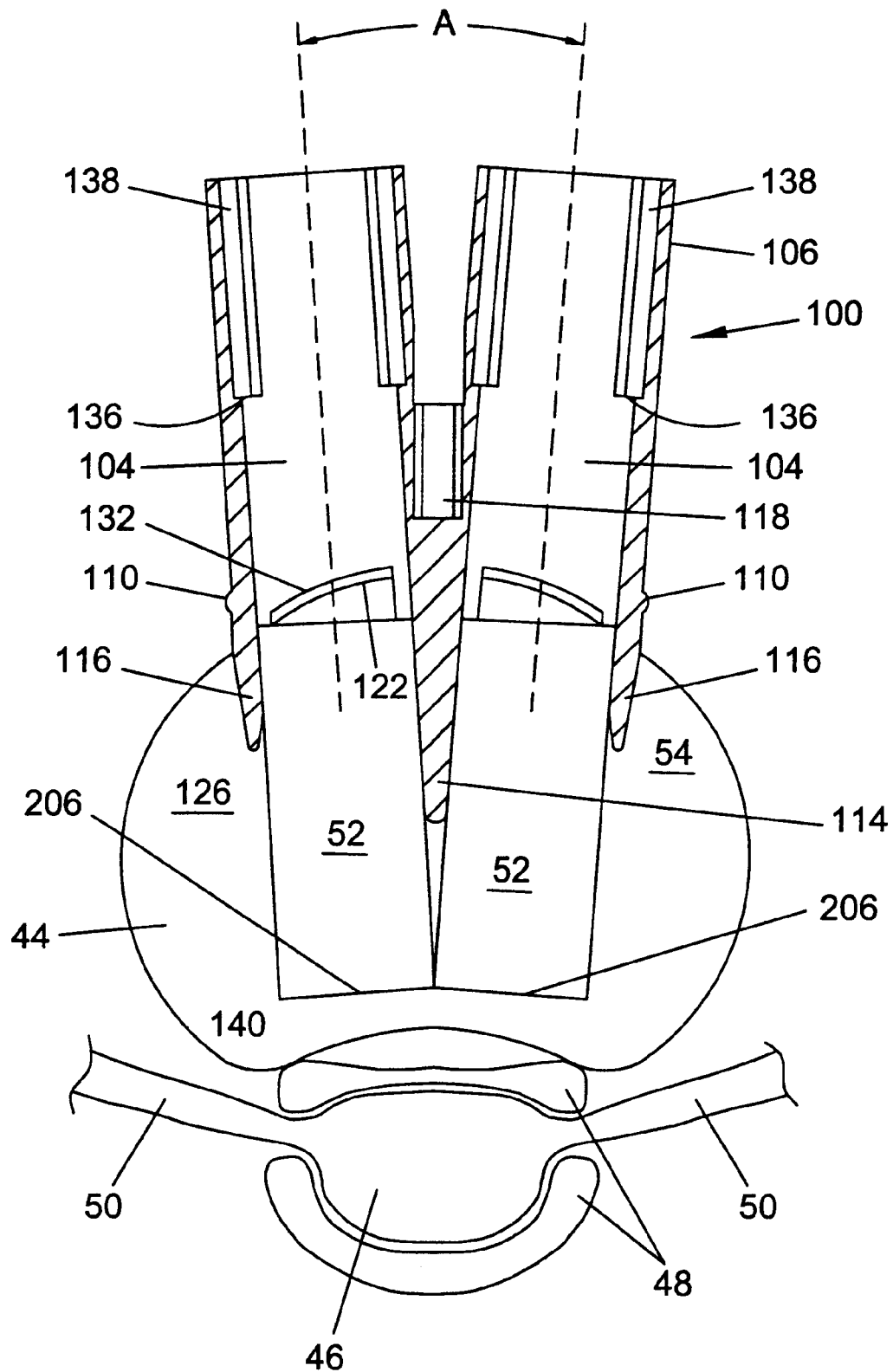
FIG. 11 is a representation of implants inserted into disc space in an angulated orientation using an embodiment of a holder.

FIG. 11 depicts a cross sectional view of an embodiment of a holder 100 inserted between a pair of vertebrae 54 (only one vertebra shown). The holder 100 may include angulated conduits 104 that allow insertion of a pair of implants 52 in an angulated orientation within a disc space 44. Angulated implants 52 may provide a more stable fusion of vertebrae 54. In addition, angulated implants 52 may be less likely to protrude from posterior side 140 of the disc space 44 to press on nerves 50 exiting the spinal canal 46. The angle A, located between a center line of a first conduit 104 and a centerline of an adjacent conduit, may vary from 0 to about 30 degrees, preferably the angle A is less than about 20 degrees, and more preferably, the angle A is less than about 10 degrees. If the angle A is 0 degrees, then the adjacent conduits 104 are parallel.

Figure 14:
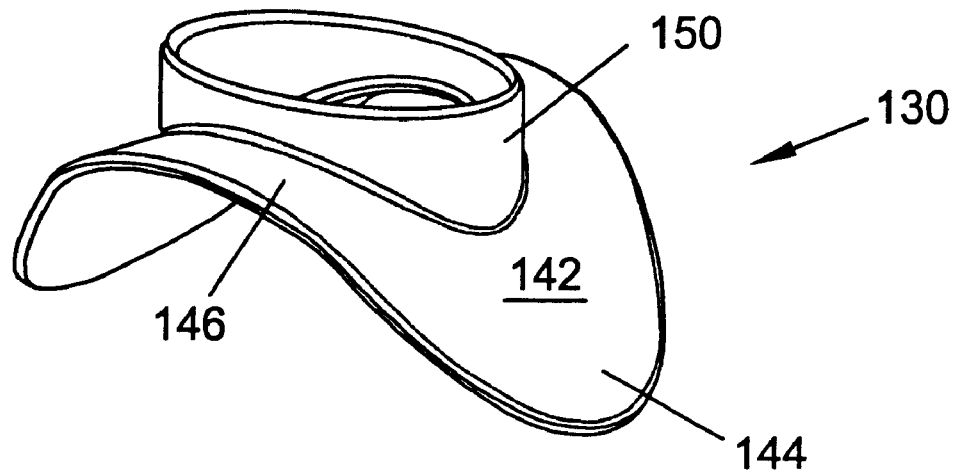
FIG. 14 is a perspective view of an embodiment of a holder flange.
Figure 15:
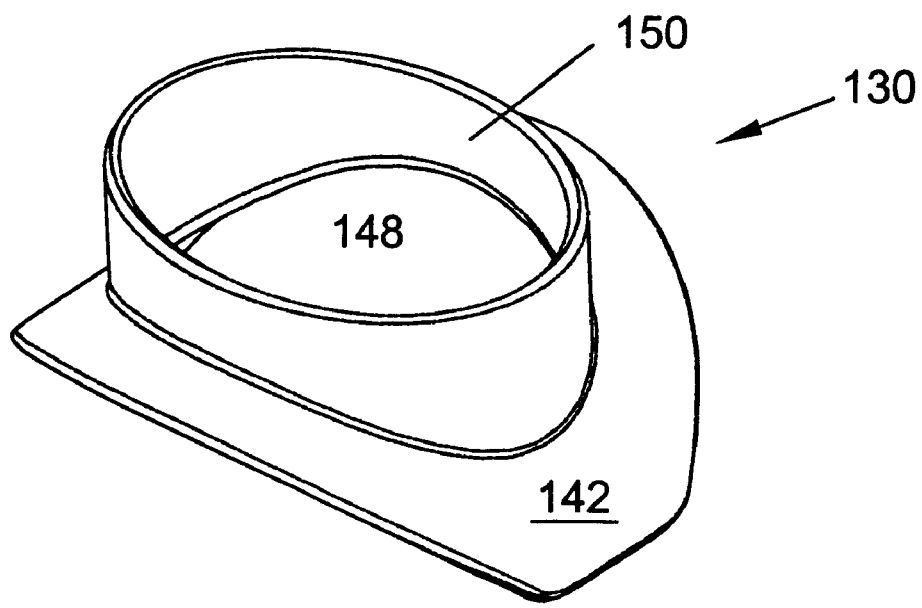
FIG. 15 is a perspective view of an embodiment of a holder flange.

FIGS. 12–15 show some flange embodiments. A flange rim of a holder may support a flange 130. The flange 130 may serve to support and protect blood vessels and other tissue placed upon the flange close to the body of the holder. As depicted in the flange embodiments of FIGS. 12–14, brim 142 of the flange 130 may include wide portions 144 and narrow portions 146. The wide portions 144 may provide extra protection and a support area on the sides of the holder where the blood vessels are most likely to be placed. In other flange embodiments, such as the flange embodiment depicted in FIG. 15, the flanges 130 may have substantially constant width brims 142 or constant width brims around central openings 148. A flange rim 110 of a holder 100 (depicted, for example, in FIG. 4) may be a stop that limits the depth that the flange may be positioned on the body 102 of the holder. As depicted in FIG. 14 and in FIG. 15, a flange 130 may have collar 150 to provide a large contact surface between the flange and the body of the holder.

A shape of a brim 142 of a flange 130 may conform to a shape of anterior surfaces of vertebrae so that a snug fit against the vertebrae is established during a spinal fusion procedure. The snug fit may help prevent tools used during the procedure from contacting and potentially damaging tissue adjacent to a holder. The flange 130 may be made of a semi-rigid, elastic material. The flange 130 may be flexible enough to be easily positioned under tissue and blood vessels adjacent to a pair of vertebrae during an implant insertion procedure. The flange 130 may be rigid and strong enough to resist movement and tearing during the procedure. A collar 150 of a flange 130 may conform to a shape of a holder body to provide a connection between the holder and the flange that inhibits movement of the flange relative to the holder.

Figure 16:
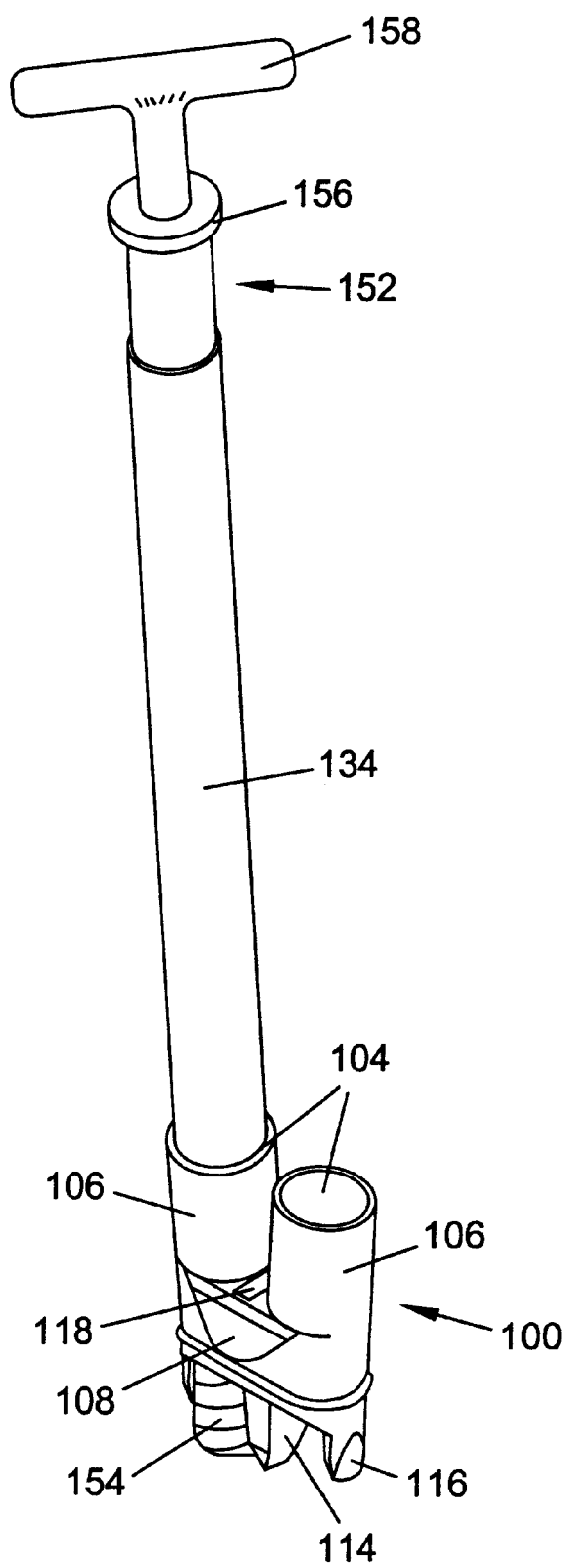
FIG. 16 is a perspective view of a holder embodiment with an inserted protective sleeve, a driver and attachment.

FIG. 16 depicts an embodiment of a holder 100 with protective sleeve 134, driver 152, and attachment 154. An embodiment of an attachment 154 may include a shaft that releasably couples to the driver 152. The driver 152 may be coupled to the attachment 154 by threading, quick release, or other connecting method. The attachment may be, but is not limited to, a drill, a tap, a chisel mechanism or an implant inserter. In other embodiments, an attachment and the driver may be permanently coupled together to form a single unit.

Figure 17:
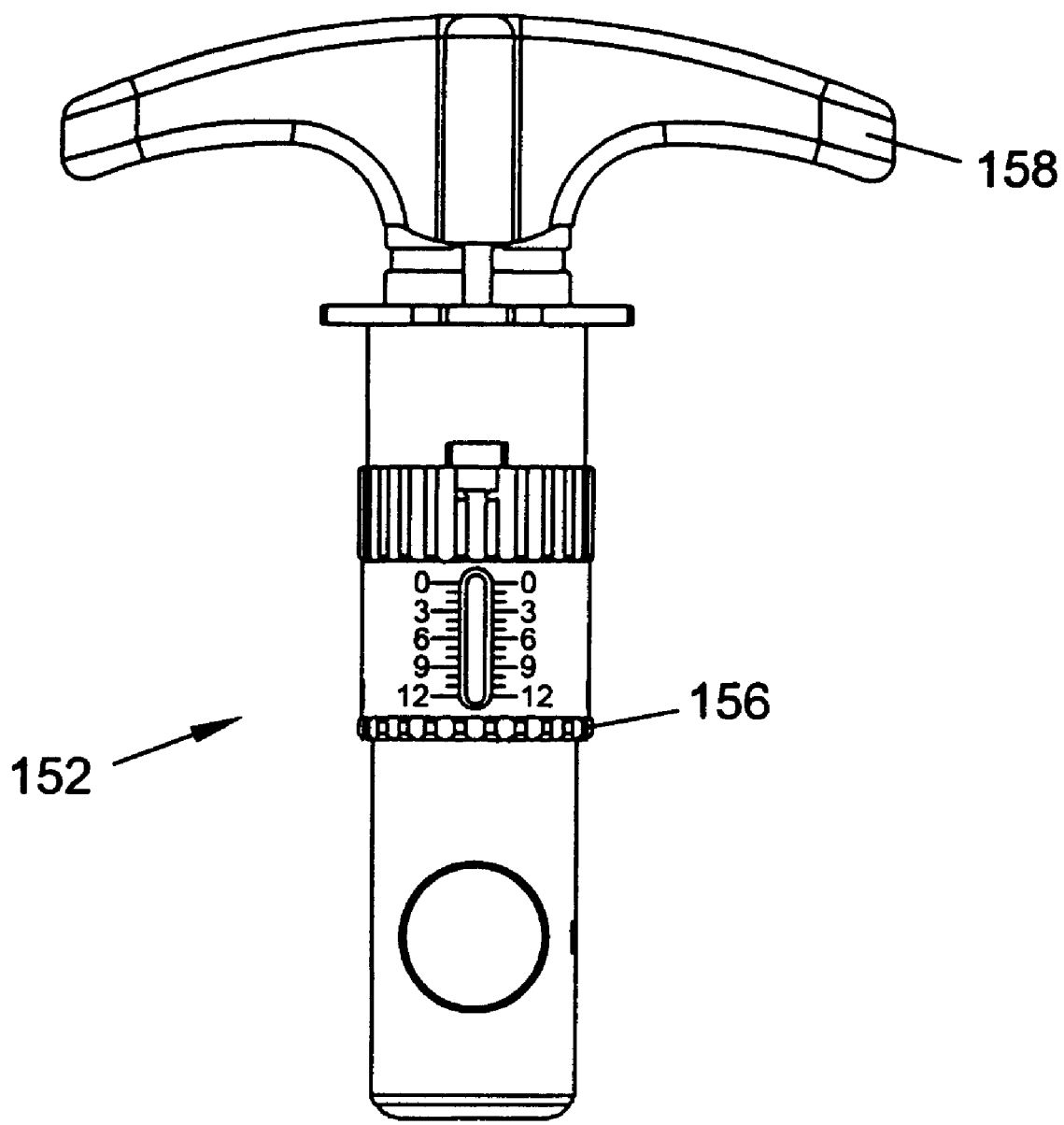
FIG. 17 depicts an embodiment of an adjustable driver for an attachment.

A protective sleeve 134 may be inserted in a conduit 104 of a holder 100. A driver 152 and attachment 154 may be inserted into the sleeve 134. At least a portion of the driver 152 that slides within the sleeve 134 may have a diameter substantially equal to an inside diameter of the sleeve 134 to maintain alignment of the driver and the attachment 154 relative to the holder 100. Stop 156 may serve to limit an insertion depth of the driver 152 into the sleeve 134. The stop 156 may also limit an insertion depth of the attachment 154 into a disc space. In some embodiments, stop 156 may be adjustable to allow a user the ability to set a specific insertion depth. FIG. 17 depicts an embodiment of an adjustable driver 152. The driver 152 may have handle 158 that allows the attachment 154 to be rotated.

Figure 18:
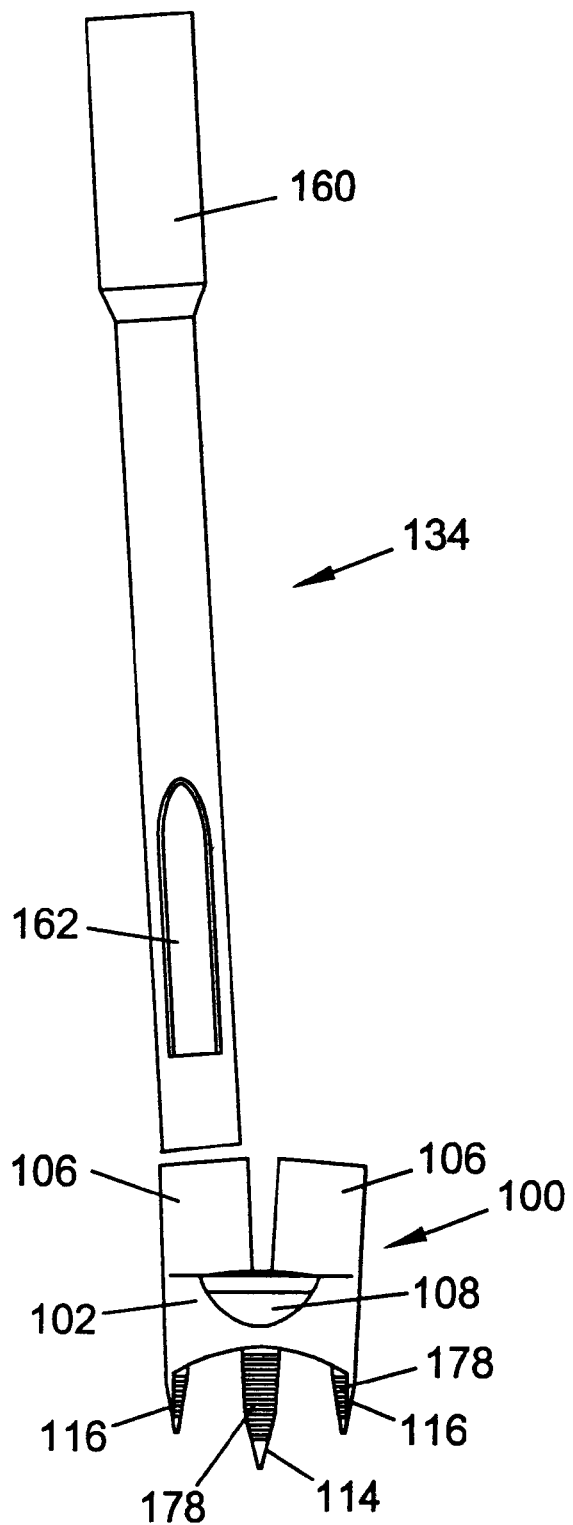
FIG. 18 is a front view of a holder embodiment prior to insertion of a sleeve embodiment within the holder.

FIG. 18 depicts an embodiment of a protective sleeve 134 prior to insertion into an embodiment of a holder 100. The protective sleeve 134 may include widened portion 160 at an end of the sleeve. The widened portion 160 may receive a driver or tool having a complementary wide portion that tightly fits within the widened portion. The sleeve 134 may include view-port 162 to provide improved visibility of a surgical site during an implant insertion procedure. The view-port 162 may be a window, a slot, or other opening in a portion of the sleeve 134 that provides increased visibility of the surgical site during the procedure. Material, such as removed portions of disc, may be removed from the surgical site through the view-port 162. A rongeur or other grasping instrument may be inserted through the view-port 162 to remove material from the surgical site without having to insert an instrument through the entire length of the sleeve 134 and without having to remove the sleeve from the holder 100. The proximity of the view-port 162 to the surgical site may allow the rongeur or other grasping instrument to be a standard sized instrument instead of a specially made long instrument. A specially made long instrument might be required if the grasping instrument were inserted through the entire length of the sleeve.

FIGS. 19a–19e illustrate steps included in a spinal fusion procedure using an embodiment of a holder 100. A discectomy may be performed to remove a portion of disc 45 to create a disc space between adjacent vertebrae 154 that allows for insertion of initial distractors. An initial distractor may include a shaft, a cylindrical portion and a distractor tip. The shaft of an initial distractor may couple to a handle that allows the distractor tip of the initial distractor to be easily positioned at a desired location within a disc space. The distractor tip may have a first width that is less than a second width. For example, a 12 millimeter initial distractor may have a distractor tip that has a small width of 10 millimeters and a large width of 12 millimeters. The handle may be a "T"-handle and the shaft may fit within the handle so that the large width of the distractor tip substantially aligns with a long axis of the handle. The small width of the initial distractor may be positioned between adjacent vertebrae using the handle. The handle may be rotated approximately 90° to form a separation distance between the vertebrae substantially equal to the large width of the distractor tip. The orientation of the handle relative to the vertebrae may function as an indicator that informs the user of the position of the initial distractor. Initial distractors may be located within a disc space so that the initial distractors extend through holder conduits when the holder is inserted into the disc space. A further discectomy may be performed to create room for distractor 114 and lateral distractors of the holder 100.

Figure 19C:
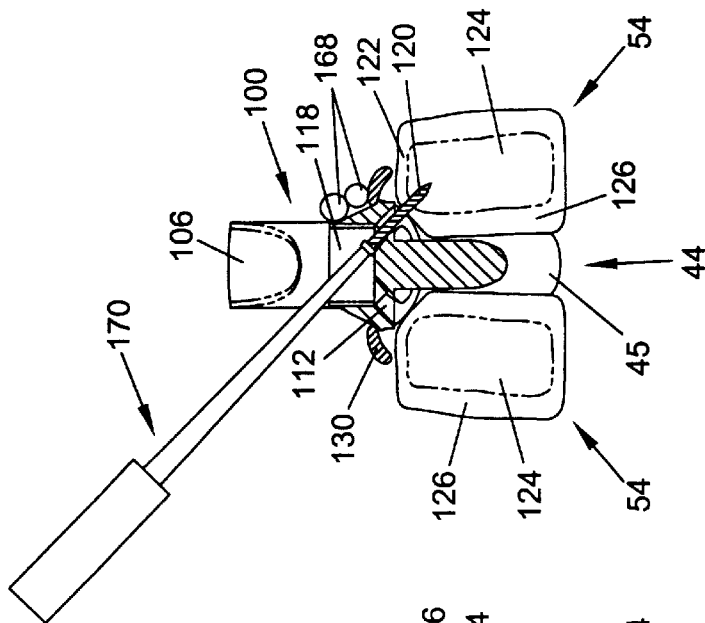
Figure 19B:
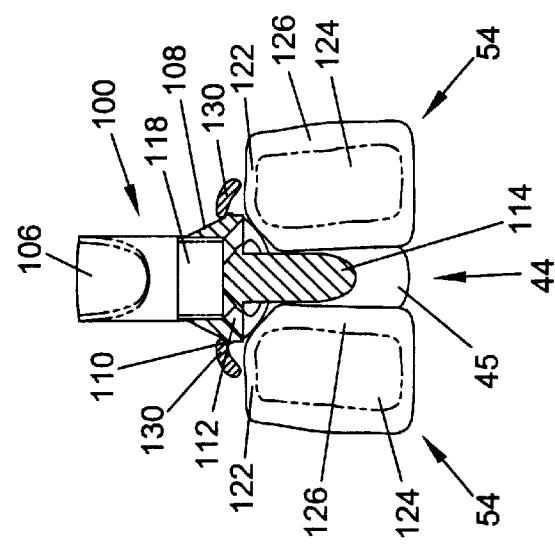
Figure 19A:
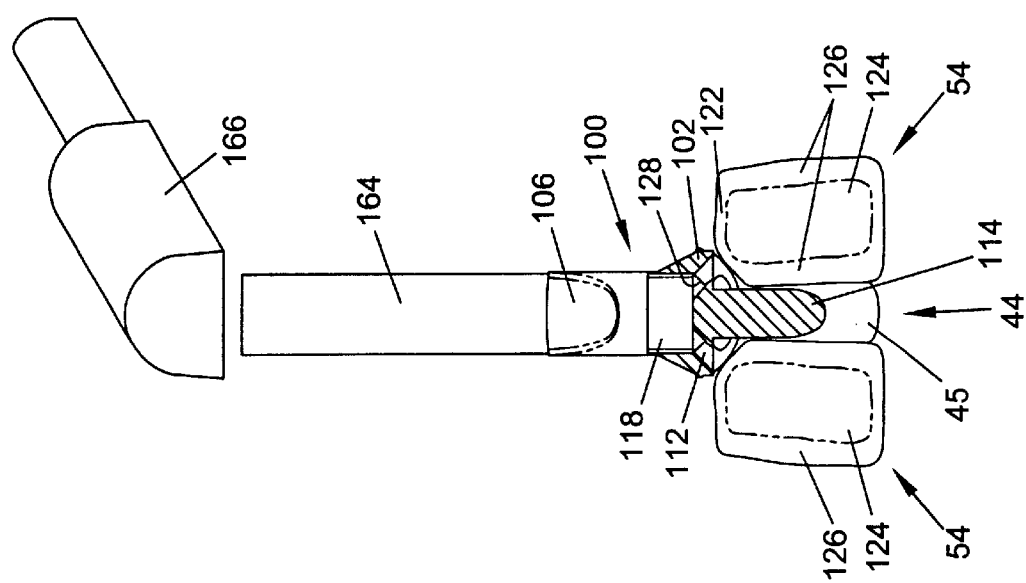

In FIG. 19a, holder 100 is shown being inserted into disc space 44 between adjacent vertebrae 54. Distractor 114 may be driven into the disc space 44 by striking insertion device 164 with mallet 166. Insertion device 164 may fit in holder conduits against the conduit shoulders. Alternately, insertion device 164 may fit between conduits in slot 118 to provide a contact surface with the holder 100. The insertion device 164 may be coupled with holder 100 prior to insertion into the surgical cavity, and may be used as a handle for inserting and positioning holder 100 by the surgeon prior to and during hammering. Distractor 114 may separate vertebrae 54 as the holder is driven into the disc space 44 by the mallet 166. The distractor 114 may widen the disc space 44 to the desired width for the procedure. Holder 100 may be hammered with the mallet 166 until the bottom of the body 102 makes contact with the end caps 122 of the adjacent vertebra 54.

Figure 20:
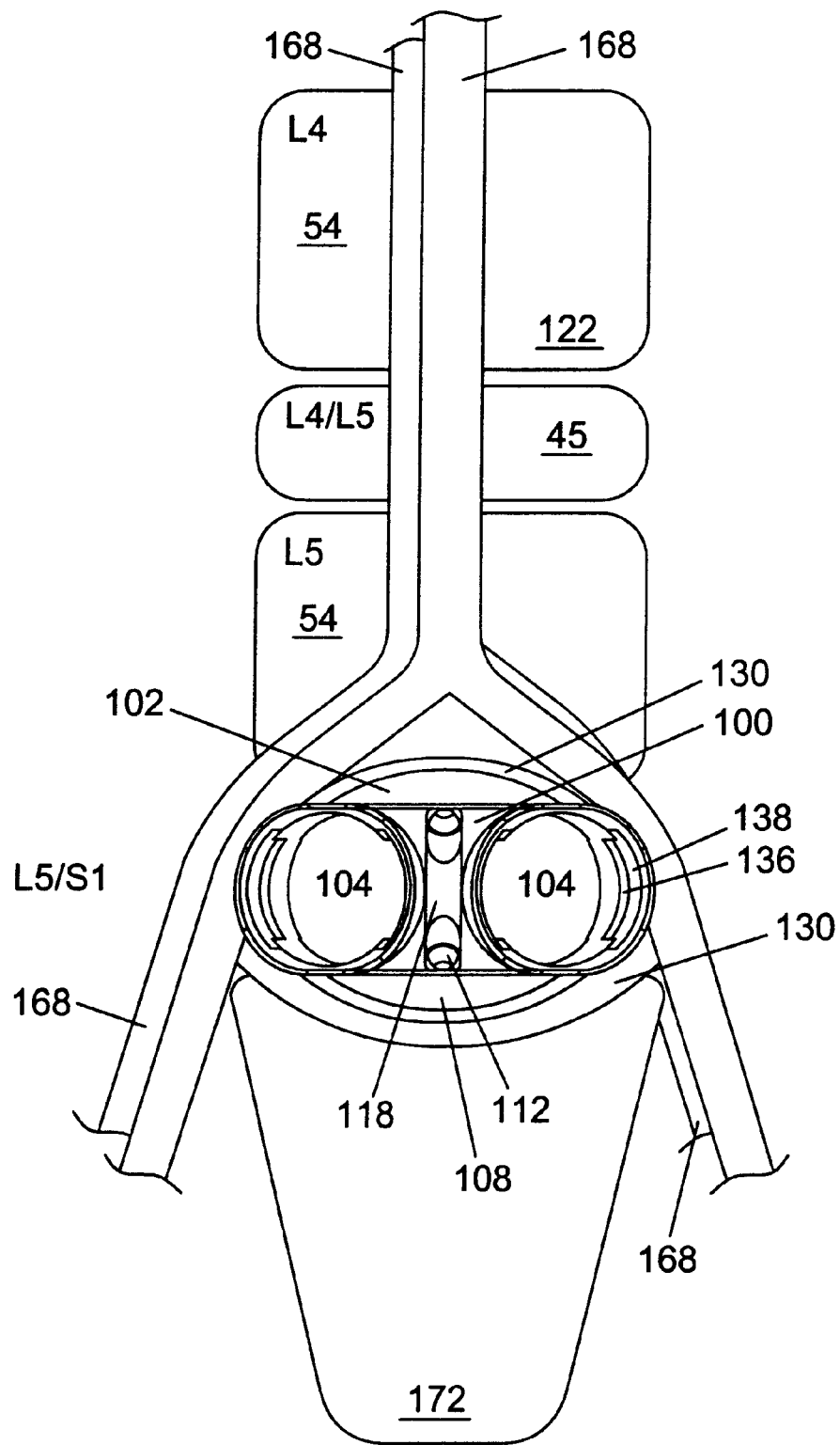
FIG. 20 illustrates the positioning of major blood vessels around one embodiment of a holder during a L5/S1 fusion procedure.
Figure 21:
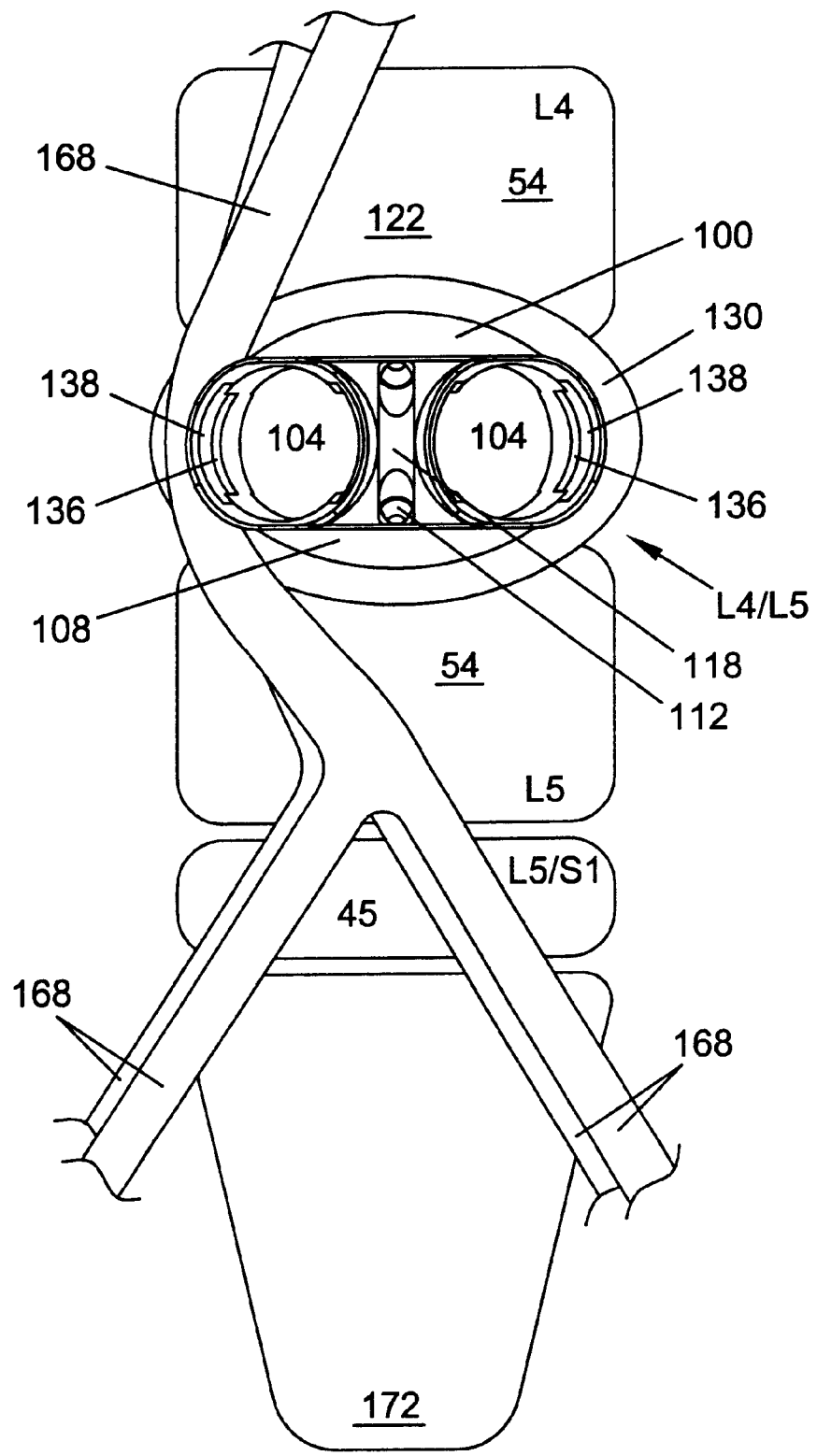
FIG. 21 illustrates the positioning of major blood vessels around one embodiment of a holder during a typical L4/L5 fusion procedure.

In FIG. 19b, holder 100 has been hammered into the disc space 44 to a desired depth. Optional flange 130 may then be slipped over the top of holder 100 to fit snugly against flange rim 110. After flange 130 is installed, blood vessels 168, such as the aorta and vena cava, which are retracted to one side during the installation of the holder 100, may be placed over flange 130 next to body 102 (as depicted in FIG. 20 and FIG. 21). The shape of flange 130 may serve to protect the blood vessels 168 from being pinched, nicked or cut during the remainder of the spinal fusion procedure. Body 102 may be formed with smooth and curved outer surfaces that have no sharp corners to further protect blood vessels 168 and tissue.

FIG. 19c shows the insertion of optional fasteners 120 in fastener holes 112, through end caps 122 and into cancellous bone 124 of vertebrae 54. Angling of fasteners 120 into cancellous bone 124 may avoid vertical penetration of the fastener deep into the end plates 126; thus helping to prevent weakening of the endplates near where implants are positioned. A head of fastener driver 170 may fit into slot 118 to contact a fastener 120. The slot 118 may protect surrounding soft tissues should the head of the driver 170 slip off the fastener 120. Slot 118 may also help contain a fastener 120 should the fastener be dropped during the insertion process. In some embodiments, the heads of fasteners 120 may include hexagonal or star shaped slots for receiving a corresponding driver 170. In some embodiments, driver 170 may include a bent or bendable shaft to facilitate the angled insertion of the fasteners 120 in the fastener holes 112. In some embodiments, the shaft of driver 170 may be long enough to allow the surgeon to turn the driver above the surgical cavity while the head of the driver is coupled to the head of a fastener 120. In some embodiments, a fastener 120 may be coupled to the driving head of driver 170 to help prevent dropping the fastener into the surgical cavity during installation.

In FIG. 19d, protective sleeve 134 is inserted in one of the conduits of the holder 100. An attachment 154, such as a drill head, may be coupled to driver 152. The attachment 154 and driver 152 may be inserted into the protective sleeve 134. Stop 156 may serve to limit insertion depth of the attachment 154 into disc space 44. Handle of the driver 152 may be rotated when the attachment 154 contacts a vertebra 54 to remove portions of disc and portions of vertebral end plates 126. Flange 130 and the sleeve 134 may protect adjacent blood vessels 168 from contacting the attachment 154 during formation of a hole for an implant.

An implant 52 that is to be inserted into a hole formed in a disc space may be any type of implant, including but not limited to, a cage or an allograft bone dowel. The implant may be packed with bone graft material, such as harvested iliac crest bone, allograft bone, and/or synthetic bone graft material. The implant 52 may be a threaded implant or an unthreaded implant.

In spinal fusion procedures using threaded implants, after a hole for an implant is drilled, driver 152 may be removed from sleeve 134, and a drill head may be replaced with a tap. The tap and the driver 152 may be inserted into the sleeve 134, through holder 100 and into a disc space 44. A handle of the driver 152 may be rotated to form threading in walls that define a previously formed implant hole. The driver 152 and tap may be removed from the sleeve 134. A threaded implant 52 may be coupled to an implant inserter, which may be coupled to the driver 152. The implant 52, inserter and driver 152 may be inserted into the sleeve 134. The driver 152 may be rotated to thread the implant 52 into the prepared threaded hole. FIG. 19e depicts a threaded implant 52 during insertion into a threaded opening. The implant 52 may be released from the implant inserter, and the inserter and driver 152 may be removed from the sleeve 134. A second implant may then be inserted through the other conduit in the holder 100 by following the same procedure of forming a hole for the implant and inserting the implant in the hole.

In spinal fusion procedures using unthreaded implants, after a hole is drilled, an unthreaded implant may be coupled to an end of an implant insertion instrument. The implant insertion instrument may be inserted through protective sleeve 134 and holder 100 into a disc space 44. A mallet (not shown) may be used to strike a proximal end of the implant insertion tool to drive the implant between vertebrae 54. The implant may be released from the insertion instrument. A second implant may then be inserted through the other conduit of the holder 100 by following the same procedure of forming a hole and inserting an implant in the hole.

After insertion of both implants, a last used instrument and sleeve 134 may be removed from holder 100. The holder 100 may then be removed from the vertebrae by removing fasteners 120 that couple the holder to the vertebrae 54. A removal tool may be coupled to the holder 100. A slap hammer may be coupled to the removal tool. A slide of the slap hammer may be impacted against a stop to remove the holder from the vertebrae 54.

An advantage of using a holder 100, such as the holder illustrated in FIGS. 19a–19e is that the instruments and protective sleeve 132 may be removed at any time during the procedure without affecting the alignment or spacing of the holder 100. Fixing the holder 100 to the vertebrae with fasteners 120, and inserting the protective sleeve 132 into the holder 100 only when necessary may minimize the risk of misalignment of implants 52 during a spinal fusion procedure.

Although the above description describes insertion of cylindrical implants, implants having non-circular cross sectional geometries may be inserted using holders, sleeves and instruments that allow formation of a properly shaped opening in a disc space and insertion of an implant into the opening. In an embodiment of a holder, conduits in the holder may have substantially rectangular cross sectional shape adapted to allow insertion of parallepiped shaped implants. Insertion tools that form an opening in a disc space for the holder may include a drill to form an initial opening and a chisel instrument to shape the opening formed by the drill into a shape that will accept the implant.

FIG. 20 illustrates the positioning of major blood vessels 168 around a dual-conduit holder 100 during an L5/S1 fusion procedure. Holder 100 is shown inserted in disc space (L5/S1) between vertebra 54 (L5) and sacrum 172 (S1). The bifurcation of major blood vessels 168 (the aorta and vena cava) typically is proximate vertebra L5. The right branch and left branch of major blood vessels 168 are shown separated and placed over holder flange 130. In some patients, the bifurcation point of the major blood vessels 168 may be located higher or lower than proximate the L5 vertebra. An irregularly located bifurcation point of the major blood vessels 168 may require the branches of the major blood vessels to be routed around one side of holder 100.

FIG. 21 illustrates the positioning of major blood vessels 168 around a holder 100 during an L4/L5 fusion process. Holder 100 is shown inserted in disc space (L4/L5) between adjacent vertebrae 54 (L4 and L5). The bifurcation of major blood vessels 168 typically is proximate vertebra L5. The major blood vessels 168 are shown placed over holder 100 upon flange 130. The blood vessels may be placed on either side of holder 100.

The configuration of holder 100 and the added protection of flexible flange 130 may serve to protect the blood vessels 168 from being nicked during the spinal fusion procedure. In addition, the body 102 of holder 100 may be curved and may lack sharp corners or edges to further protect the blood vessels 168 and other tissue from abrasion. Protecting the blood vessels 168 is critical in a spinal fusion procedure, as the aorta is a major artery and the vena cava is a major vein. Even a tiny nick in either blood vessel 168 is potentially catastrophic, and must be repaired quickly. A nick in the vena cava is particularly problematic because the vena cava has thinner walls than the aorta, making the vena cava easier to nick and harder to repair than the aorta.

Figure 22:
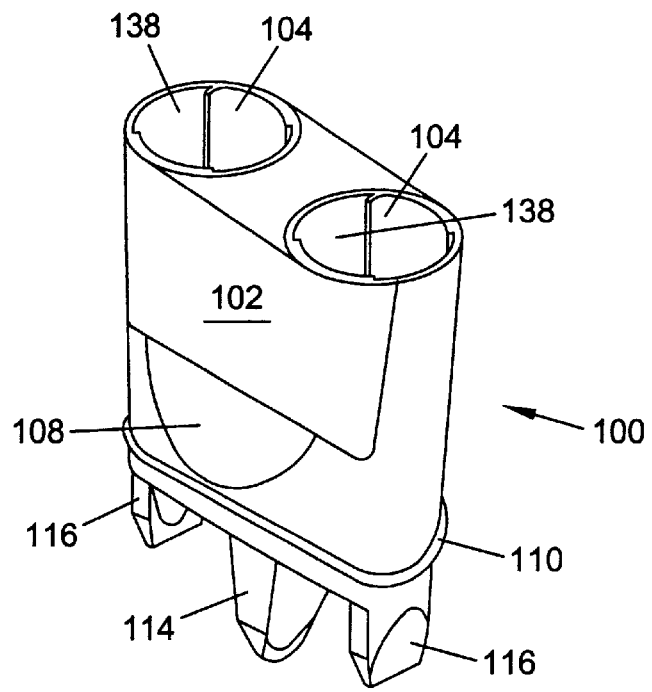
FIG. 22 is a perspective view of an embodiment of a holder without conduit extenders.
Figure 23:
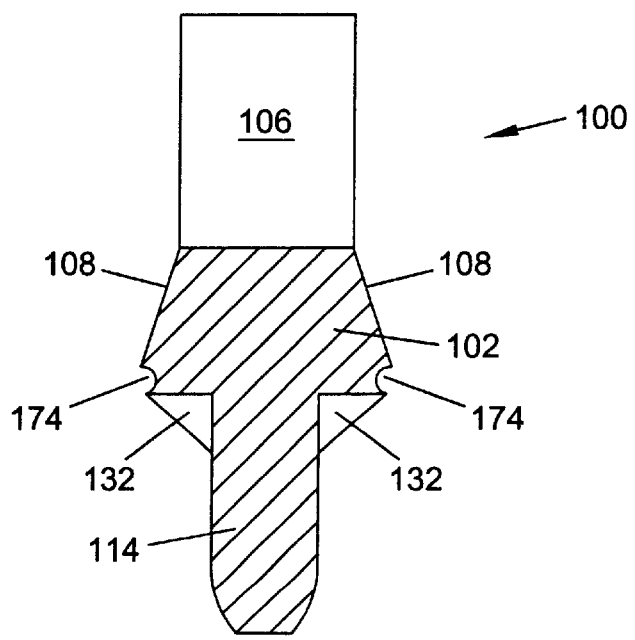
FIG. 23 is a cross sectional view of an embodiment of a holder having a flange groove.
Figure 24:
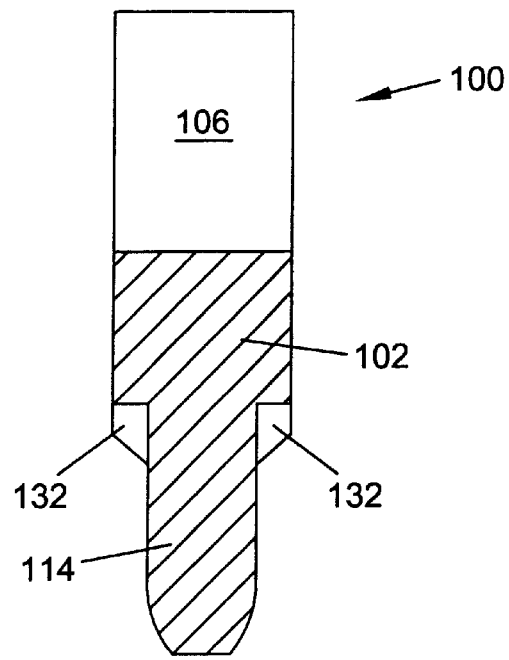
FIG. 24 is a cross sectional view of an embodiment of a holder without body flare.

FIG. 22 depicts a holder 100 wherein the body 102 does not include conduit extenders. FIG. 23 depicts a cross sectional view of a holder 100 with flange groove 174. The flange groove 174 may support an inner edge of a flange to hold the flange at a desired position on the body 102. FIGS. 23 and 24 depict cross sectional views of holders 100 without fastener holes. FIG. 24 also depicts the holder 100 without a flared portion and without a flange rim or a flange groove.

Figure 25:
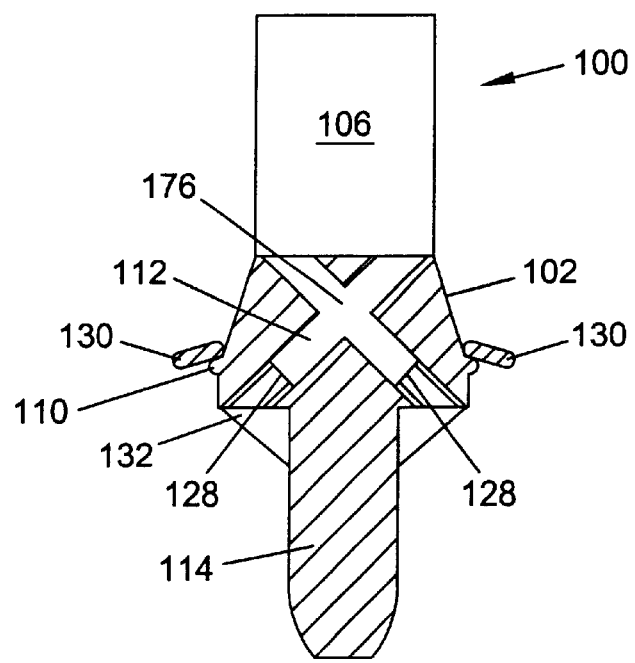
FIG. 25 is a cross sectional view of an embodiment of a holder with an alternative fastener hole arrangement.

FIG. 25 depicts a cross sectional view of a holder embodiment with an alternate fastener hole 112 arrangement. In this embodiment, fastener holes 112 extend between conduits within the body 102. The fastener holes 112 may intersect at point 176 and then exit near an outer edge of a lower portion of the body 102. The fastener holes 112 may include shoulders 128 to limit insertion depth of fasteners into the fastener holes. To use this embodiment with more than one fastener, a first fastener is inserted into a fastener hole 112 and into a first vertebra. The fastener is driven into the first vertebra until a head of the fastener is driven past the cross point 176. Then, a second fastener is inserted into the remaining fastener hole and the fastener is driven into a second, adjacent vertebra. Both fasteners may be further inserted into the vertebrae until the fastener heads contact the shoulders 128.

Figure 26:
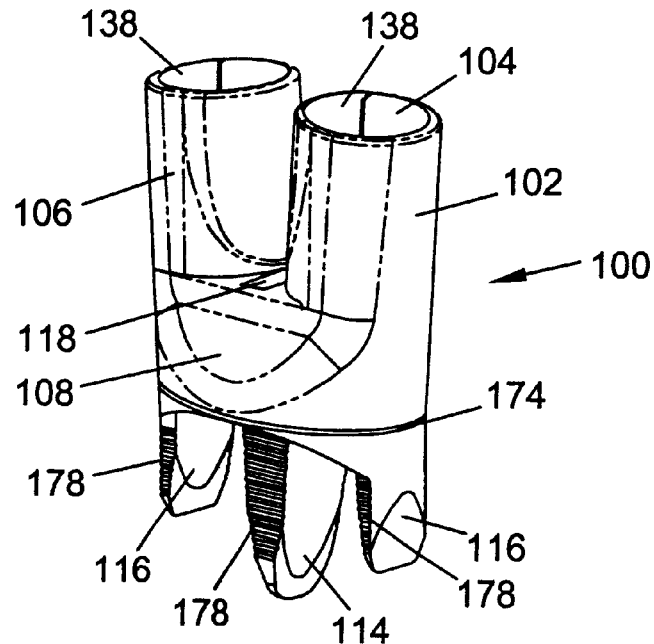
FIG. 26 is a perspective view of an embodiment of a holder having serrated distractors.

FIG. 26 shows an embodiment of a holder 100, which has serrations 178 on outer edges of distractor 114 and on outer edges of lateral distractors 116. Serrations 178 may maintain proper alignment and may inhibit the distractors 114, 116 from backing out of vertebrae after the holder 100 is inserted into a disc space during an implant insertion procedure. In alternate holder embodiments, distractors 114 and/or lateral distractors 116 may include surface roughening. The surface roughening may promote increased frictional engagement between the distractors 114 and/or 116 and vertebrae or an adjacent disc as compared to smooth surface distractors. Surfaces of the distractors 114 and/or 116 may be roughened by any convenient manufacturing technique, including but not limited to, serrating the surfaces, scoring the surfaces, ball peening the surfaces, an electric discharge process, and/or fusing particles to the surfaces. Particles may be fused to the surface by melt fusion, adhesive, chemical reaction or other processes.

Figure 27:
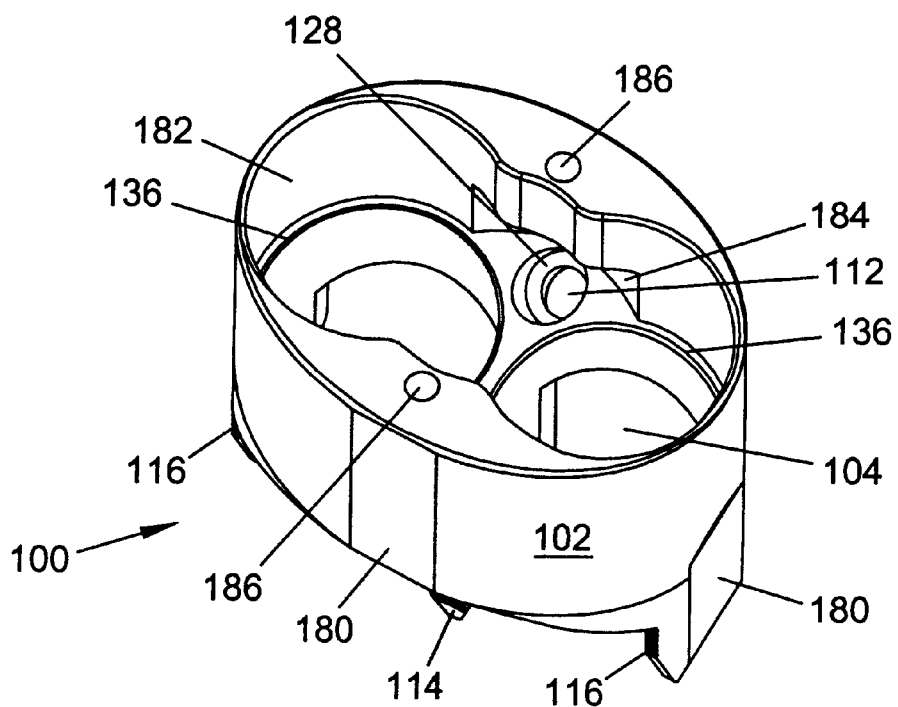
FIG. 27 is a perspective view of an embodiment of a holder having an extended upper opening and an insertion tool slot.
Figure 28:
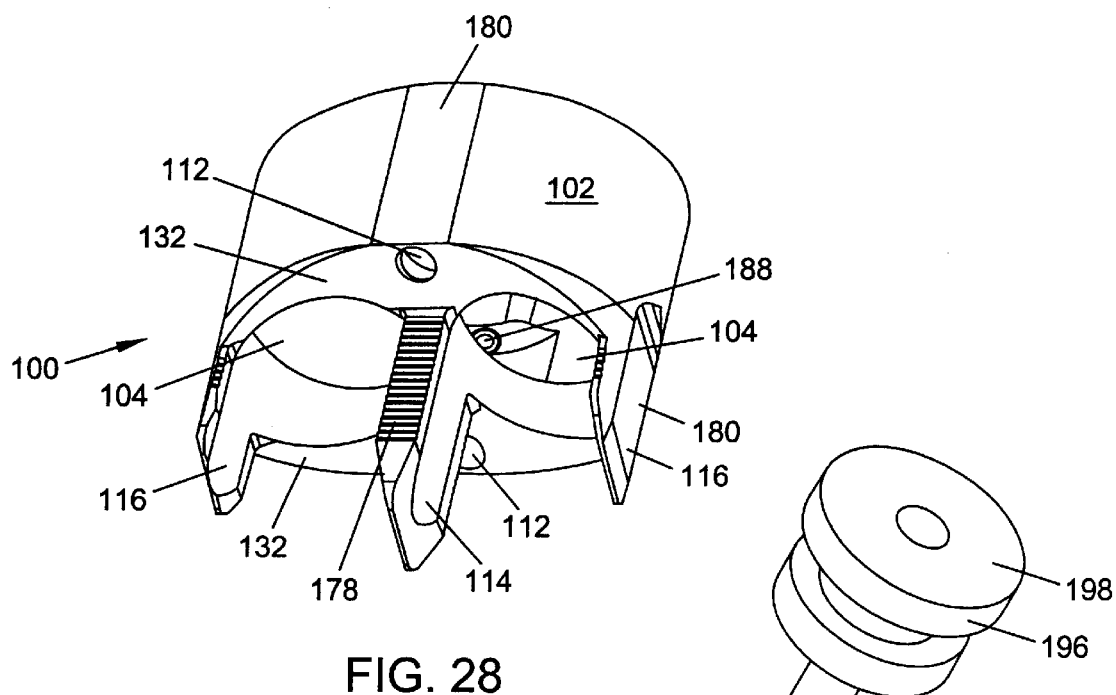
FIG. 28 is a perspective view of the holder embodiment depicted in FIG. 27 that emphasizes lower surfaces of the holder.

FIG. 27 and FIG. 28 depict perspective views of an alternate embodiment of a holder 100. The body 102 may include flat sections 180, large top opening 182, undercut tool slots 184, spring stops 186, and balls 188. The flat sections 180 may make the holder 100 easier to machine during manufacturing. The holder may have large top opening 182 with conduits 104 located in a lower section of the body 102. The body 102 may have undercut tool slots 184. Coil springs may be placed in the body 102 between the spring stops 186 and the balls 188 (one shown in FIG. 28). The spring stops 186, coil springs and balls 188 form an assembly that may removably connect an insertion tool 164 to the holder 100.

Figure 29:
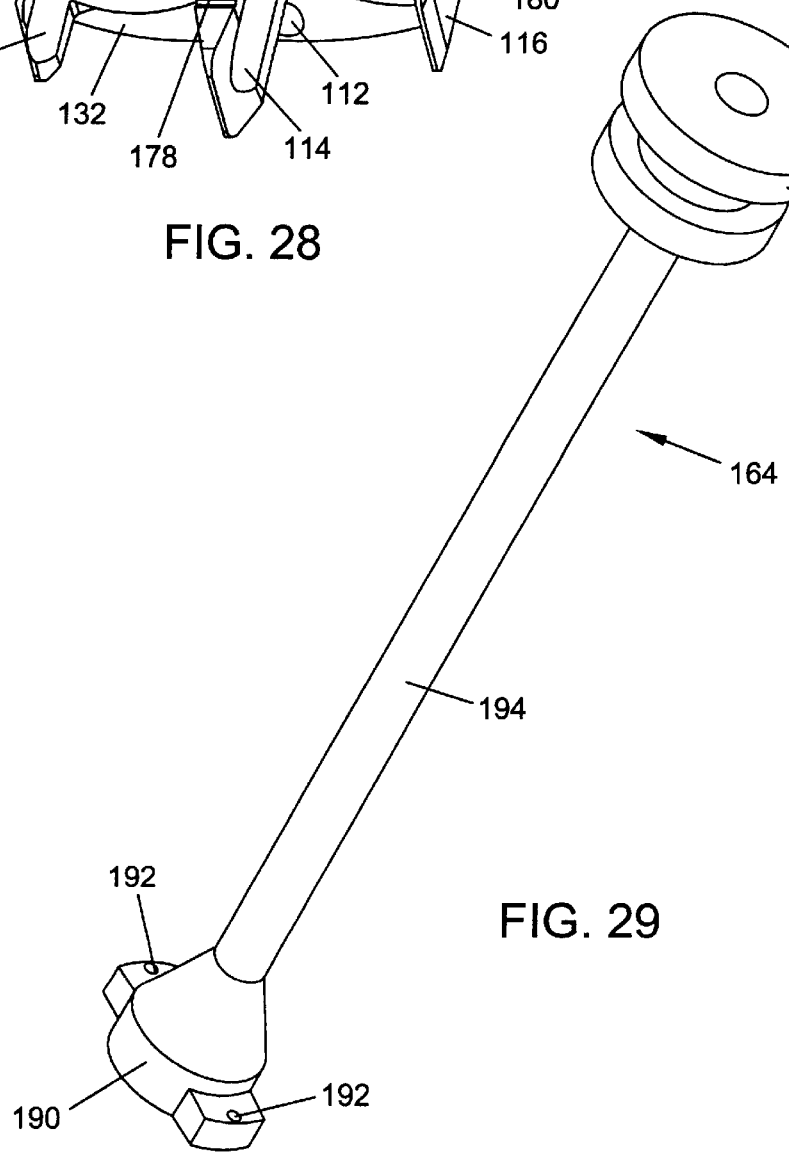
FIG. 29 is a perspective view of an insertion tool for an embodiment of a holder.

FIG. 29 depicts an embodiment of an insertion tool 164 that may be used with holder embodiments depicted in FIG. 27 and FIG. 28. The insertion tool 164 may include attachment head 190, dimples 192, shaft 194, and top member 196. The attachment head 190 of the insertion tool 164 may be inserted into a top opening 182 of a holder 100 (depicted in FIG. 27). The insertion tool 164 may be rotated approximately 90 degrees. Rotating the insertion tool 164 may force balls 188 in the holder body 102 against the coil springs within the body to compress the coil springs. When the dimples 192 align with balls 188, the springs force the balls into the dimples and attach the insertion tool 164 to the holder 100. When the holder 100 is attached to the insertion tool 164, the insertion tool may function as a handle and allows the holder to be positioned at a desired location. A mallet (not shown) may be used to strike upper surface 198 of the top member 196 to insert the holder into a disc space after the holder 100 is positioned at a desired location. To remove the insertion tool 164 from the holder 100, the insertion tool may be rotated approximately 90 degrees, and the attachment head 190 may be withdrawn from the opening 182 of the holder.

Figure 30:
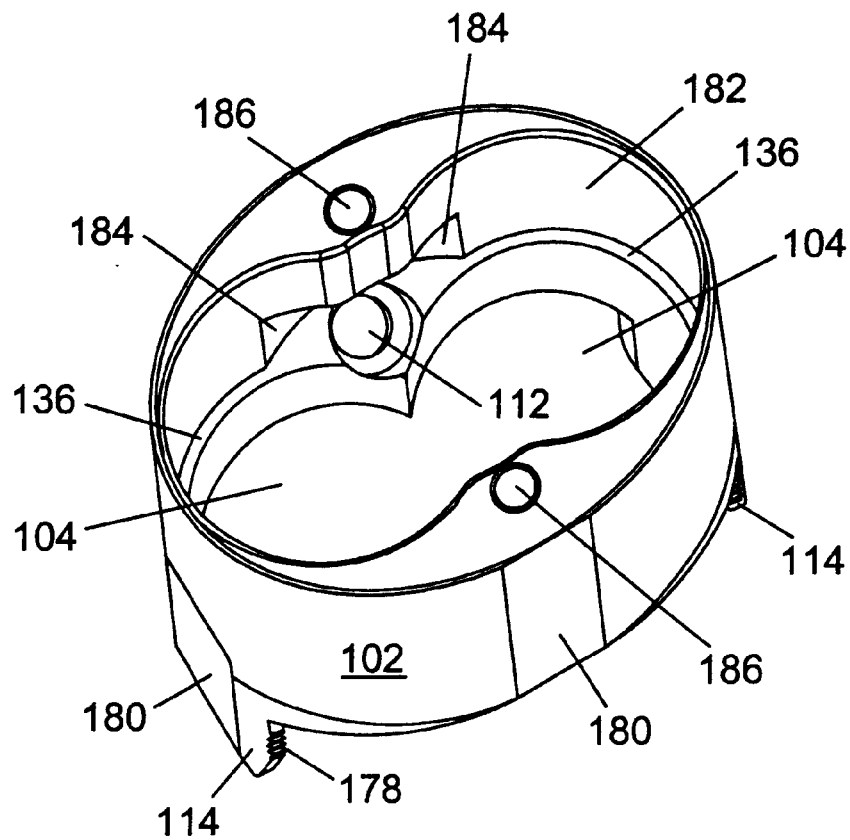
FIG. 30 is a perspective view of an embodiment of a holder having overlapping conduits.
Figure 31:
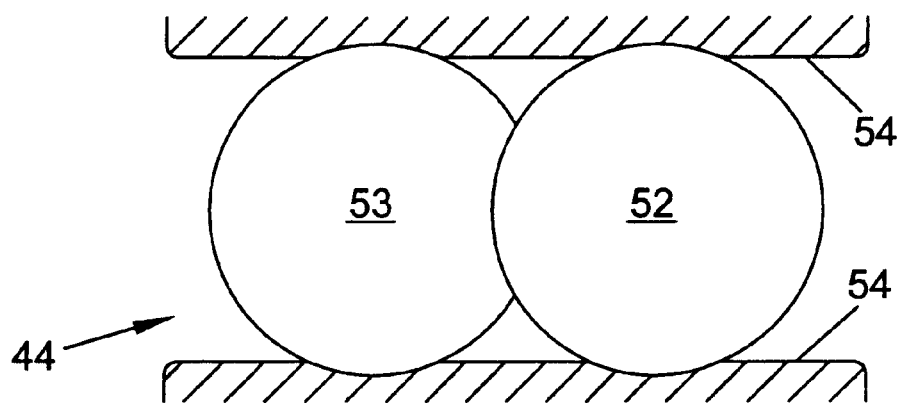
FIG. 31 is a top view of an arrangement of implants inserted into a disc space using a holder having overlapping conduits, such as the holder depicted in FIG. 30.

FIG. 30 depicts a perspective view of an embodiment of a holder 100 wherein the conduits 104 of the holder overlap. The holder has a pair of distractors 114 located at opposite sides of the body 102. FIG. 31 shows a representation of implants 52, 53 inserted in a disc space 44 with the embodiment of a holder 100 shown in FIG. 30.

Figure 32:
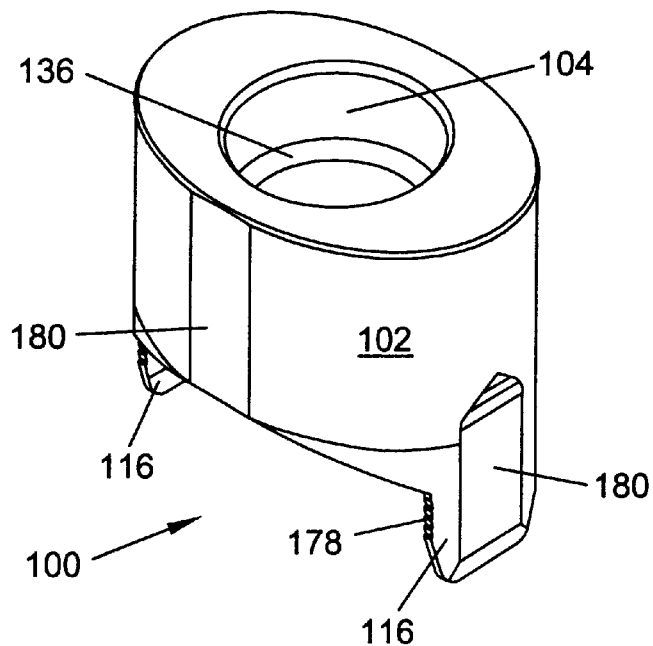
FIG. 32 is a perspective view of an embodiment of a single conduit holder.

FIG. 32 depicts an embodiment of a holder 100 having one conduit 104 extending through body 102 of the holder. The holder 100 may have a pair of distractors 116 located at opposite sides of the conduit 104. The holder 100 may have fastener holes in the body that allow fasteners to attach the holder to vertebrae during a spinal fusion procedure.

Figure 33:
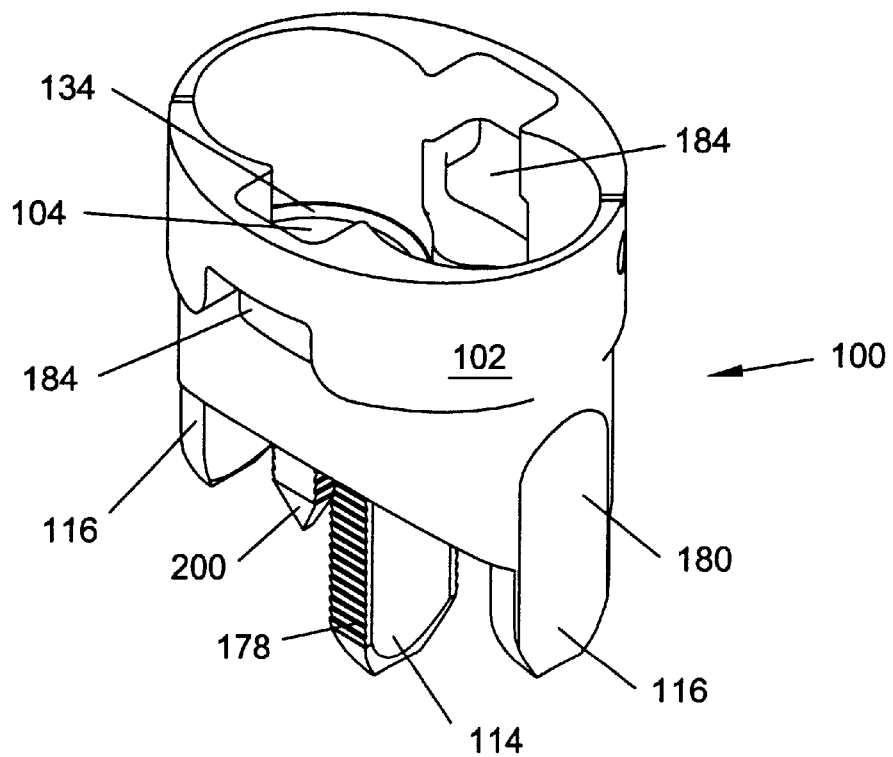
FIG. 33 is a perspective view of an embodiment of a dual conduit holder that includes tangs for coupling the holder to vertebrae.
Figure 34:
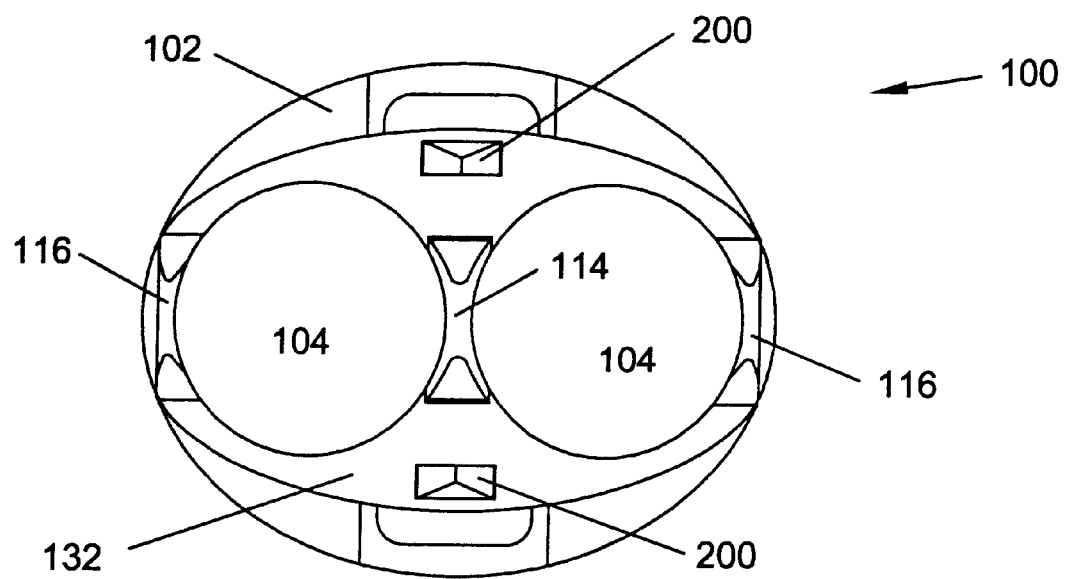
FIG. 34 is a bottom view of the holder embodiment depicted in FIG. 33.
Figure 35:
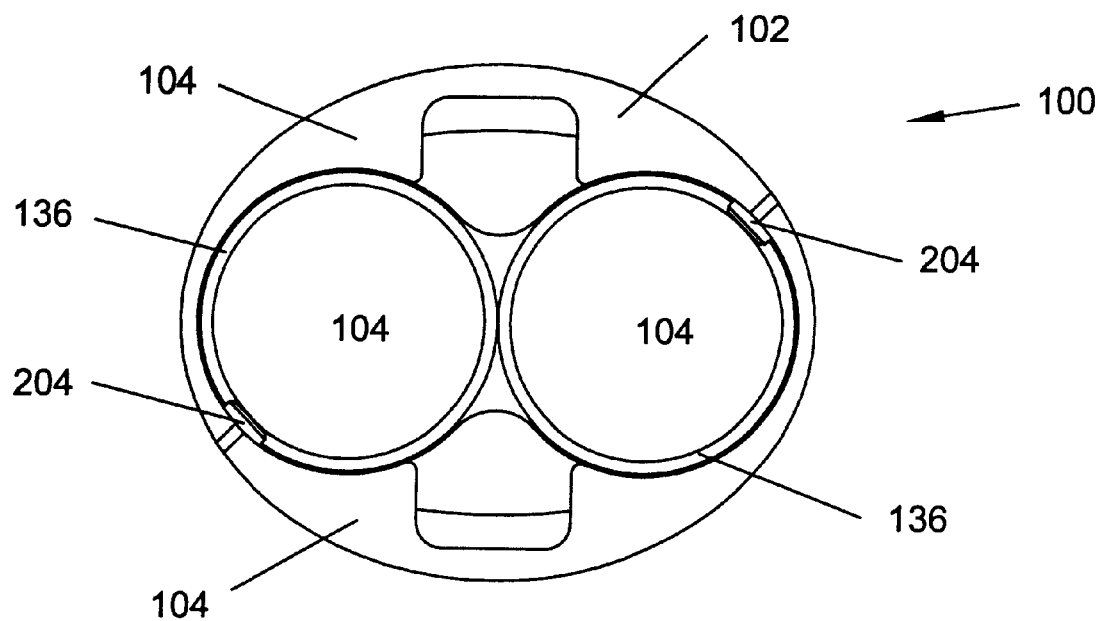
FIG. 35 is a top view of the holder embodiment depicted in FIG. 33.

FIGS. 33–35 depict an embodiment of a dual conduit holder 100 that includes tangs 200. Surfaces of the holder body 102 may be contoured to reduce the weight of the holder 100. The holder 100 may include tangs 200 extending from bottom surface 132 of the holder as depicted in FIG. 33 and in FIG. 34. Tangs 200 may be driven into vertebrae to securely couple the holder 100 to vertebrae during an implant insertion procedure. Surfaces of the tangs 200 may be serrated and/or textured to form a strong, secure engagement between the holder 100 and the vertebrae. The tangs 200 may replace fastener holes and fasteners that are used with other holder embodiments. Tangs 200 may be advantageous because the use of tangs 200 may eliminate the need for a fastener driver to couple a holder to adjacent vertebrae with fasteners.

Figure 36:
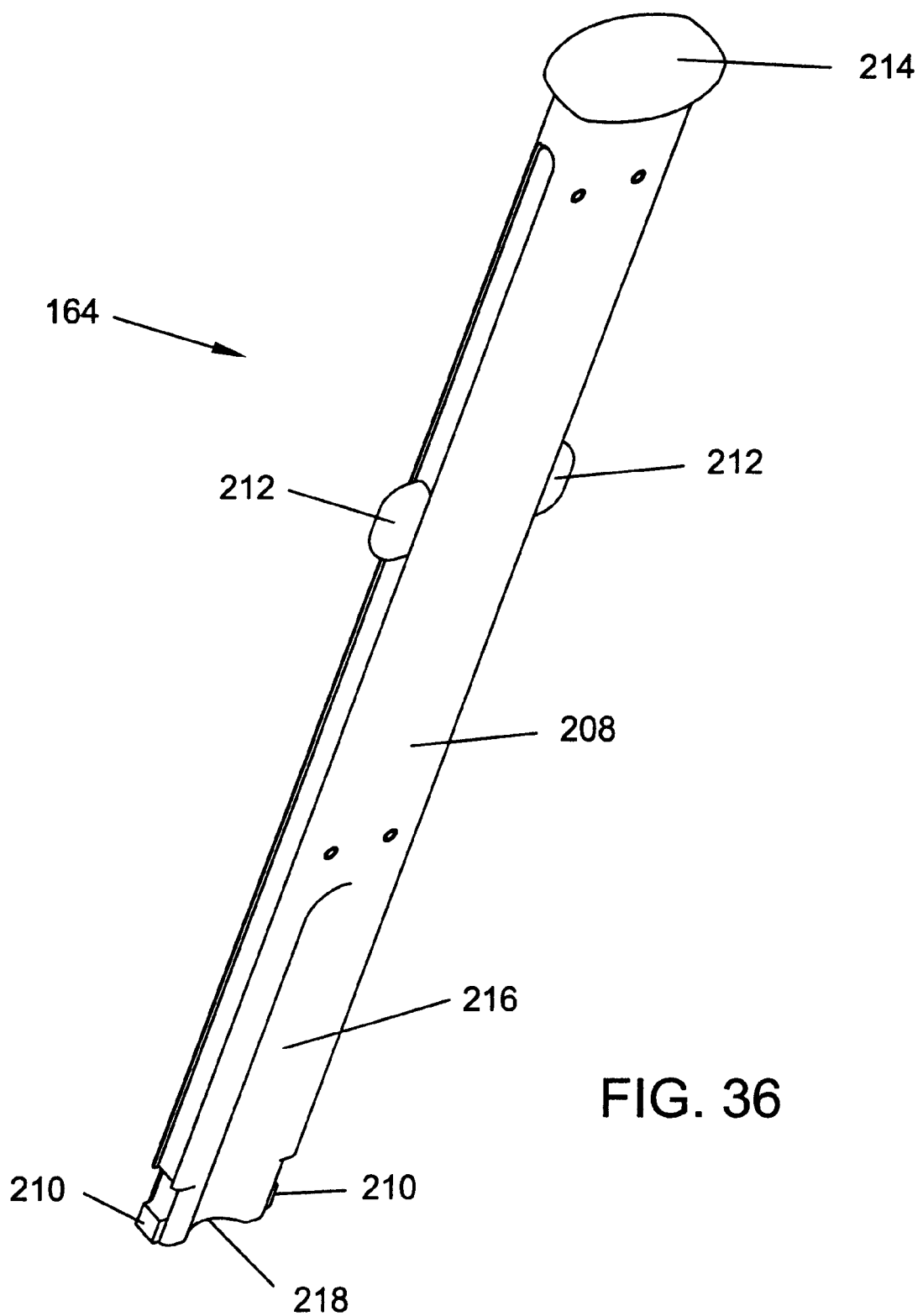
FIG. 36 is a perspective view of an insertion tool that may be used to couple the holder embodiment of FIG. 33 to a pair of vertebrae.

Tool slots 184 (depicted in FIG. 33) in the body 102 of a holder may extend completely through the body to further reduce the weight and to couple to an embodiment of an insertion tool 164, such as the insertion tool depicted in FIG. 36. The tool slots 184 may also couple to a removal tool 202, such as the removal tool depicted in FIG. 37.

Figure 39:
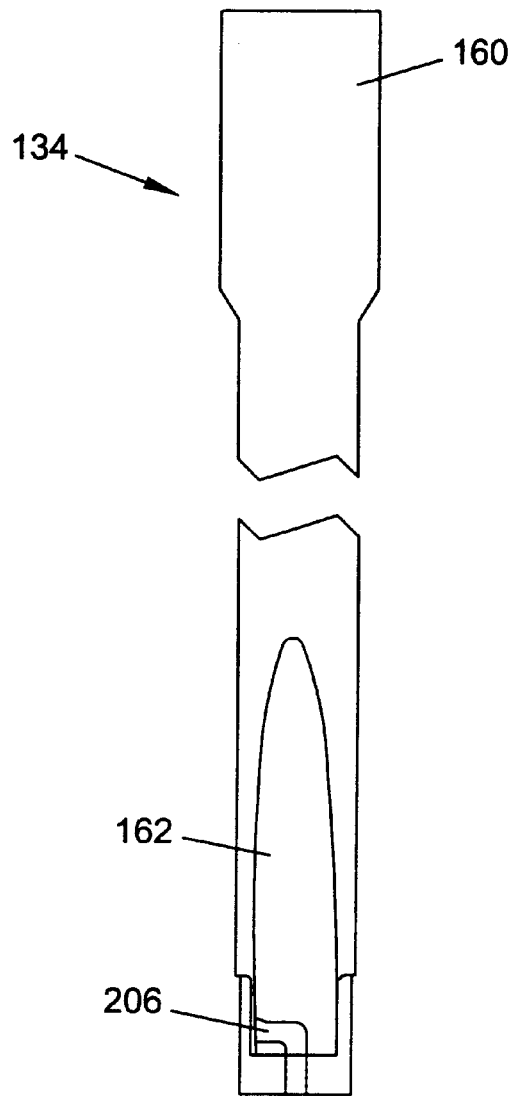
FIG. 39 is a front view of an embodiment of a sleeve that includes a view-port and a keyway that allows the view-port to be positioned in a desired location in a holder.

A holder 100 may include projections 204, as depicted in FIG. 35. The projection 202 may engage keyway 206 of a sleeve 134. A sleeve 134 having a keyway 206 is depicted in FIG. 39 and in FIG. 40. In an embodiment of the sleeve, the keyway 206 may have a upside down "L" shape. Other keyway shapes may also be utilized. When the sleeve 134 is inserted into the holder so that the projection 204 engages the keyway 206, the sleeve may be rotated to place sleeve view-port 162 in a desired orientation. The desired orientation of the view-port 162 may inhibit tissue from entering into the view-port during an implant insertion procedure. The desired orientation of the view-port when the sleeve 134 is positioned in a first conduit may be facing the adjacent conduit of the dual conduit holder 100. The keyway 206 and the projections 204 may be positioned in the body so that rotation of the sleeve by 45° may properly orient the view-port 162. Other rotational ranges may be chosen if the configuration of the keyway 206 and the position of the projections 204 are altered.

FIG. 36 shows a perspective view of an embodiment of an insertion tool 164 that may be used with a holder embodiment such as the holder 100 depicted in FIG. 33. The insertion tool 164 may include body 208 engagers 210, release 212, and top 214. Engagers of the insertion tool may be sized to couple to tool slots 184 of a holder 100, such as the holder depicted in FIG. 33. Pressing release 212 may allow one or both of the engagers 210 to move laterally within the body 208 so that the insertion tool may be inserted into or removed from the holder 100. Compression springs within the body 208 may force the engagers 210 outwards when the release is not pressed. When the engagers 210 are positioned within holder tool slots 184, the insertion tool may function as a handle that allows the holder to be easily positioned at a desired location.

A body 208 of an insertion tool 164 may be thin. The body may also include recesses 216 (only one shown). The thin body 208 and recesses may allow a holder 100, such as the holder depicted in FIG. 33, coupled to the insertion tool 164 to be placed over initial distractors that are positioned within a disc space without the initial distractors interfering with the insertion tool. To insert the holder 100 into the disc space so that the holder is coupled to adjacent vertebrae, a mallet be used to strike top 214 of the insertion tool 164. Striking the top of the insertion tool 164 may cause lower surface 218 that extends below engagers 210 to contact the holder 100 and drive the holder into the disc space. Contact of the lower surface 218 with the holder 100 allows force to be transmitted to the holder without the force being transmitted through the engagers 210. The top 214 may be struck with the mallet until tangs 200 of the holder 100 are driven into the vertebrae and bottom 132 of the holder abuts the vertebrae.

Figures 37, 38:
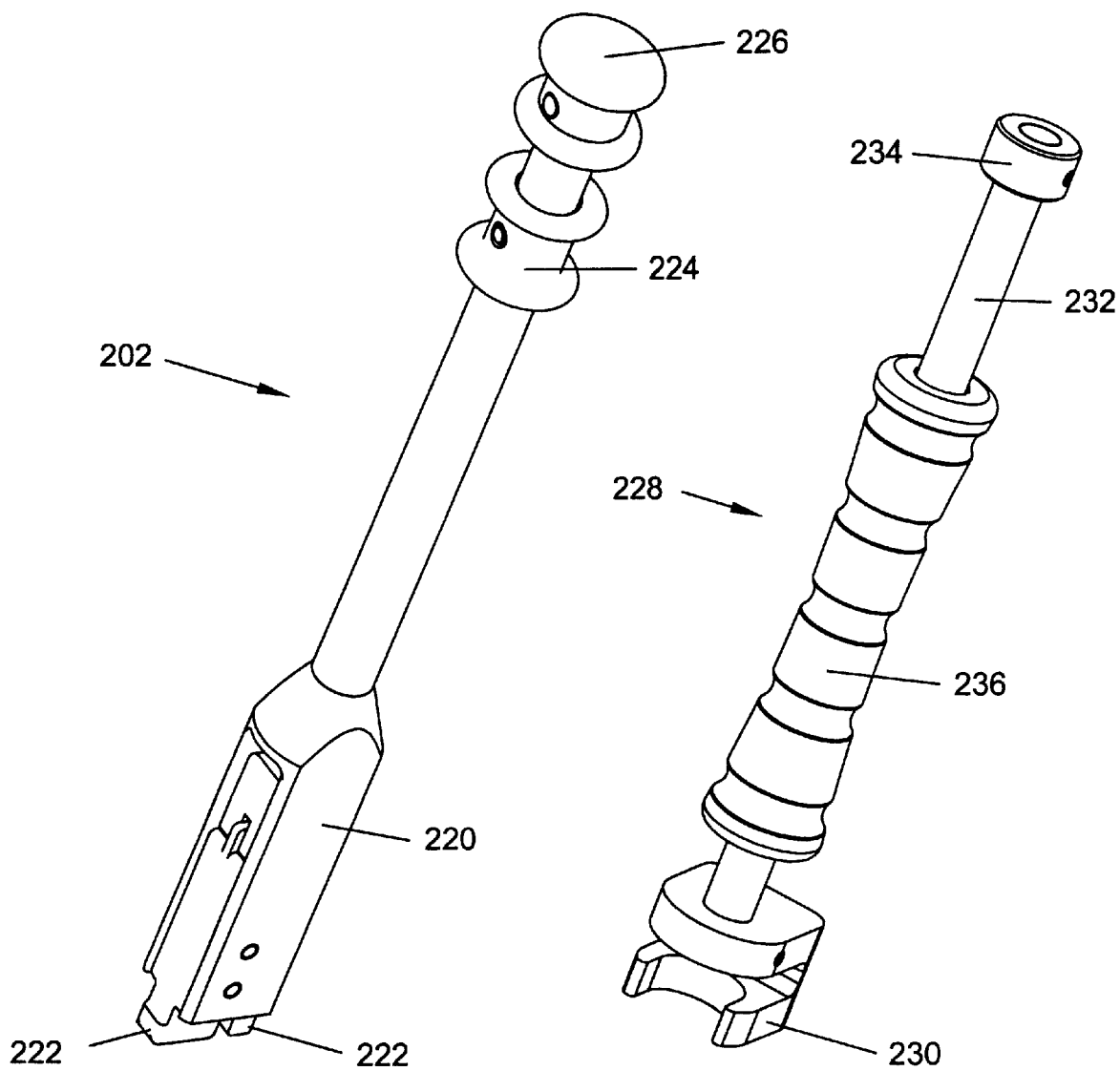
FIG. 37 is a perspective view of a removal tool that may be used to remove the holder embodiment of FIG. 33 from a pair of vertebrae.
FIG. 38 is a perspective view of an embodiment of a slap hammer that may be used with the removal tool depicted in FIG. 37.

FIG. 37 depicts a removal tool 202 that may be used to remove a holder, such as the holder 100 depicted in FIG. 33, from a pair of adjacent vertebrae. The removal tool 202 may include body 220, engagers 222, release 224, and cap 226. The engagers 222 of the removal tool 202 may be coupled to tool slots 184 of the holder 100. Grasping and pulling release 224 towards cap 226 may compress an internal spring and allow engagers 222 to move inwards within body 220. When the release 224 is pulled towards the cap 226, the removal tool may be inserted into, or removed from, the holder 100. When a user does not apply force to the release 224 to move the release towards the cap 226, the internal spring may force the release to an initial position and cause the engagers 222 to move outwards in the body 220. If the removal tool 202 is positioned within a holder when the release 224 returns to the initial position, the engagers 222 may securely couple to the holder body at the tool slots 184. Side-to-side and upward force may be applied to the removal tool 202 to disengage the holder 100 from adjacent vertebrae that the holder is coupled to. If additional force is needed to remove the holder from the vertebrae, a slap hammer may be coupled to the removal tool.

FIG. 38 depicts a slap hammer 228 that may be coupled to a removal tool to apply force to disengage a holder from a pair of adjacent vertebrae. The slap hammer 228 may include attachment 230, shaft 232, stop 234 and slide 236. The attachment 230 may be coupled to a cap of a removal tool. Upward force may be applied to the removal tool by grasping slide 236 and sliding the slide along shaft 232 to impact the slide against stop 234.

Figure 40:
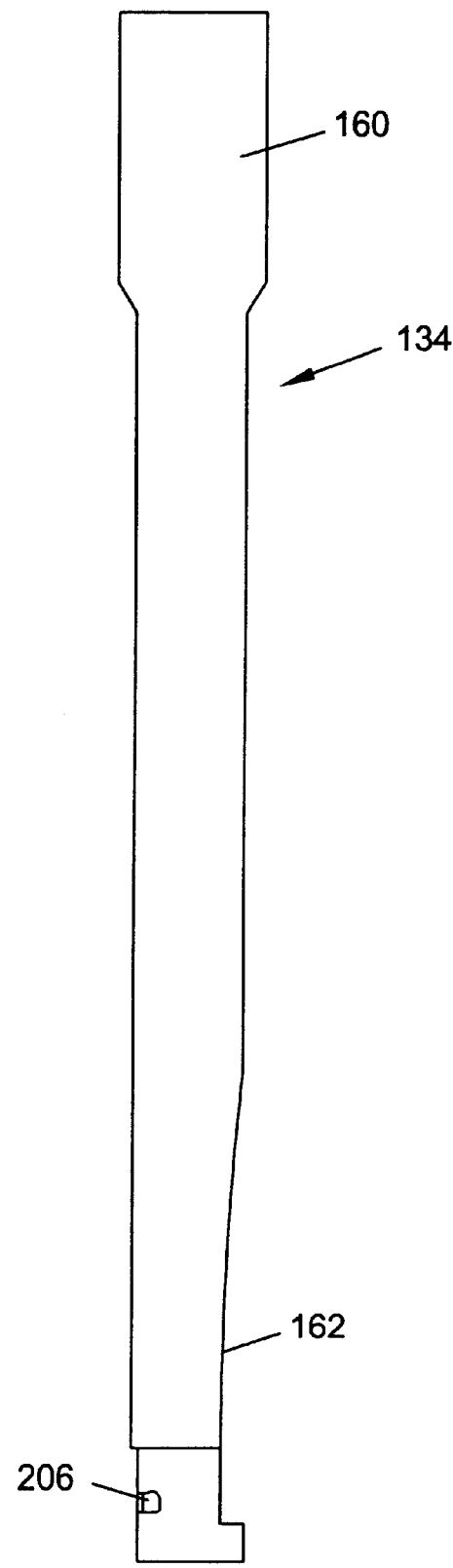
FIG. 40 is a side view of the sleeve embodiment depicted in FIG. 39.
Figure 41:
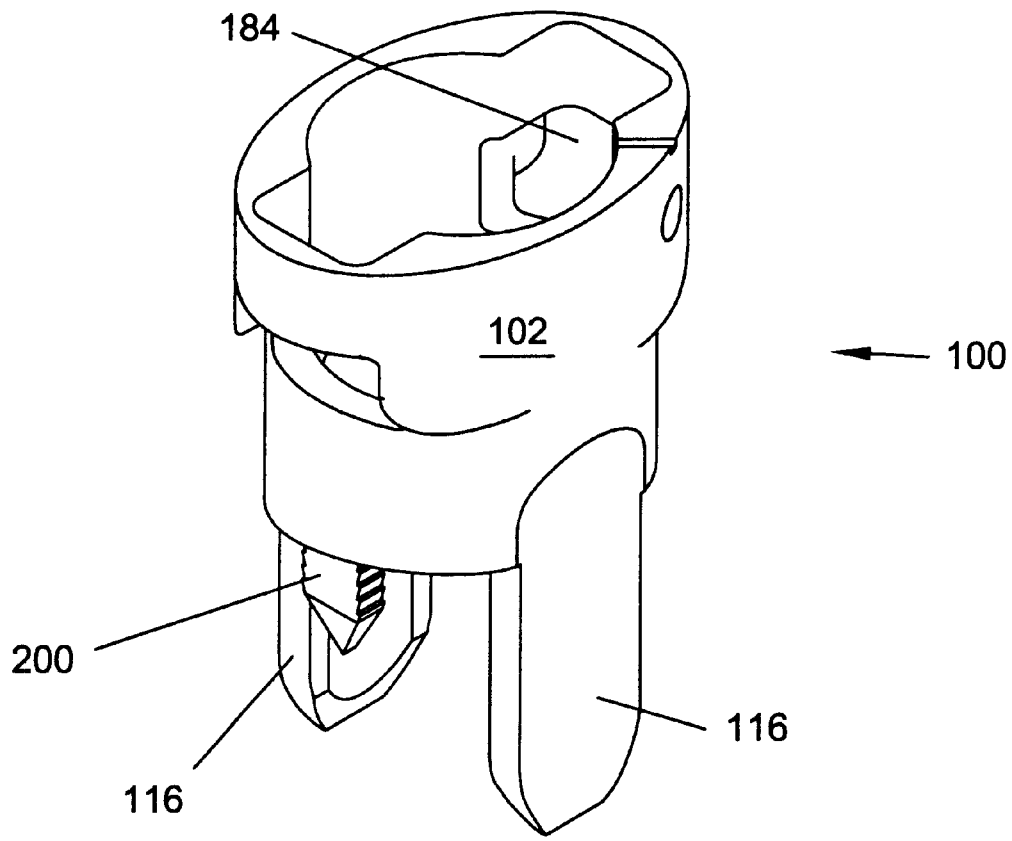
FIG. 41 is a perspective view of an embodiment of a single conduit holder that includes tangs for coupling the holder to vertebrae.
Figure 42:
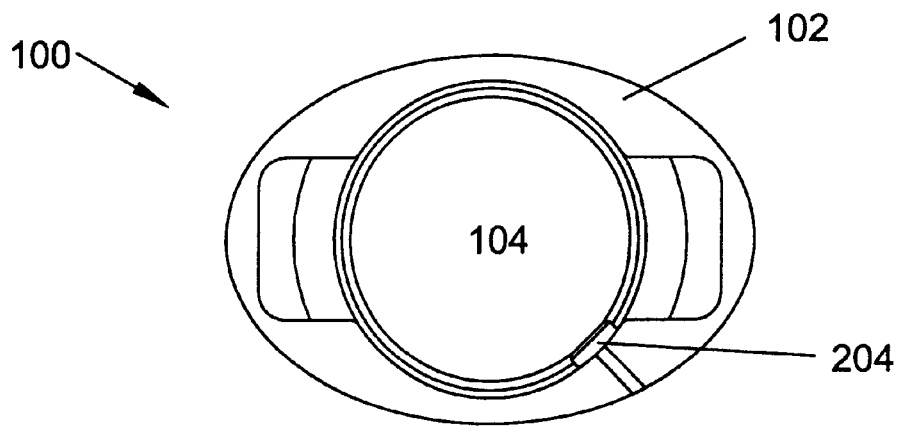
FIG. 42 is a top view of the single conduit holder embodiment depicted in FIG. 41.

FIG. 39 and FIG. 40 depict an embodiment of a single conduit holder 100. A tube may be used to couple the single conduit docking station to a pair of vertebrae. An initial distractor may be positioned within the tube during insertion of the holder 100 within a disc space. The tube may include a keyway that engages a projection 204 of the holder 100. An end of the tube may be placed against shoulder 136 of the holder 100 and rotated to couple the holder to the tube. The tube may then be used as a handle for the holder 100 to easily position the holder at a desired location. A cap may be placed on top of the tube. The cap may be struck with a mallet to drive the holder into a disc space. The mallet may be used until tangs 200 are driven into the vertebrae and bottom of the holder 100 contacts the vertebrae. Alternatively, insertion tool 164 depicted in FIG. 36 may be coupled to tool slots 184 of the holder 100. The insertion tool may be used to drive the holder into the disc space. The insertion tool 164 may be used to insert the holder 100 when an initial distractor will not contact the holder or the insertion tool. A removal tool embodiment, such as the removal tool 202 depicted in FIG. 37, may be used to remove the holder from vertebrae after an implant has been inserted into the space.

A single conduit holder 100 may include a projection 204 configured to be placed within a keyway of a sleeve. The keyway may allow the sleeve to be rotated when the sleeve is inserted into the holder 100. Rotating the sleeve may couple the sleeve to the holder 100 and position a view-port of the sleeve in a desired orientation. The desired orientation of the view-port may position the view-port so that the view-port faces towards a center of a disc space, as opposed to facing an adjacent edge of the disc space. In an embodiment, rotating the sleeve 45° may position the view-port of a sleeve in the desired orientation. Keyways of sleeves and projections 204 of holders may be configured to allow other rotation ranges for obtaining the desired orientation of viewports for the sleeves.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A holder for use with a sleeve during a spinal fusion procedure, comprising:
 a body;
 a slot in the body, the slot configured to engage an instrument;
 at least one protrusion extending from the body, the at least one protrusion configured to couple the body to a disc space between a first vertebra and a second vertebra; and
 a conduit through the body;
 wherein an end of the sleeve is removably positionable in the conduit during use, and wherein the sleeve is configured to allow tools or devices for implanting a spinal fusion device, or for preparing a patient to receive a spinal fusion device, to be inserted in the disc space through the sleeve and through the conduit.

2. The holder as defined in claim 1, further comprising a shoulder in the conduit, the shoulder configured to limit an insertion depth of the sleeve into the conduit.

3. The holder as defined in claim 1, wherein the at least one protrusion establishes a separation distance between the first vertebra and the second vertebra during use.

4. The holder as defined in claim 1, wherein the at least one protrusion comprises sides and further comprising serrations on at least one side of the at least one protrusion.

5. The holder as defined in claim 1, further comprising a projection extending from an inner surface of the body that defines the conduit, the projection configured to engage a keyway of the sleeve.

6. The holder as defined in claim 5, wherein rotation of the sleeve couples the sleeve to the body.

7. The holder as defined in claim 5, wherein the sleeve comprises a view-port, and wherein the keyway and the projection are configured to limit rotation of the sleeve in the conduit so that the view port is positioned in a set orientation when the sleeve is rotated.

8. The holder as defined in claim 7 wherein the view-port faces a center of the disc space when rotation of the sleeve is inhibited by an end of the keyway contacting the protrusion.

9. The holder as defined in claim 1, further comprising a flange, the flange having an inner edge, an outer edge, a lower surface and an upper surface, wherein the flange is positionable around the body, and wherein the flange is configured to protect tissue and vessels adjacent to the disc space during use.

10. The holder as defined in claim 9, wherein the flange is made of a semi-rigid material.

11. The holder as defined in claim 9, wherein the lower surface of the flange curves during use to substantially match curvatures of surfaces of vertebrae adjacent to the holder.

12. The holder as defined in claim 9, further comprising a rim on a portion of an outer surface of the body, wherein the rim is configured to engage the lower surface of the flange to support the flange during use.

13. The holder as defined in claim 9, further comprising a groove on a portion of an outer surface of the body, wherein the groove is configured to engage the inner edge of the flange to support the flange during use.

14. The holder as defined in claim 9, wherein the flange further comprises an elastic collar configured to conform to the shape of the body during use to support the flange during use.

15. The holder as defined in claim 1, wherein a height of the body is less than about six inches.

16. The holder as defined in claim 1, wherein a height of the body is less than about four inches.

17. The holder as defined in claim 1, wherein a height of the body is less than about two inches.

18. The holder as defined in claim 1, further comprising at least one tang that couples the body to a first vertebra.

19. The holder as defined in claim 18, wherein the tang further comprises serrations on at least one side of the at least one tang.

20. The holder as defined in claim 1, further comprising a slot in a conduit wall, the slot configured to engage a distractor on an end of the sleeve during use.

21. The holder as defined in claim 1, wherein the sleeve further comprises a view-port to provide increased visibility of a surgical site during use.

22. The holder as defined in claim 1, wherein a bottom of the body is curved to substantially conform to curvatures of vertebrae adjacent to the holder during use.

23. The holder as defined in claim 1, wherein the instrument is an insertion instrument, the insertion instrument configured to releasably engage the slot.

24. The holder as defined in claim 1 wherein the slot is an opening through the body.

25. The holder as defined in claim 1, wherein the instrument is a removal instrument, the removal instrument configured to releasably engage the slot.

26. The holder as defined in claim 1, further comprising at least one tang, wherein the at least one tang is configured to engage the first vertebra to couple the body to the vertebra.

27. The holder as defined in claim 1, wherein the conduit comprises a non-circular perimeter, and wherein the conduit is configured to guide a non-cylindrical implant into the disc space.

28. A holder for use with a sleeve during a spinal fusion procedure, comprising:
a body;
at least one protrusion extending from the body, the at least one protrusion configured to couple the body to a disc space between a first vertebra and a second vertebra;
a conduit through the body; and
a projection extending from an inner surface of the body that defines the conduit, the projection configured to engage a keyway of the sleeve;
wherein an end of the sleeve is removably positionable in the conduit during use, and wherein the sleeve is configured to allow tools or devices for implanting a spinal fusion device, or for preparing a patient to receive a spinal fusion device, to be inserted in the disc space through the sleeve and through the conduit.

29. The holder as defined in claim 28, further comprising a shoulder in the conduit, the shoulder configured to limit an insertion depth of the sleeve into the conduit.

30. The holder as defined in claim 28, wherein the at least one protrusion establishes a separation distance between the first vertebra and the second vertebra during use.

31. The holder as defined in claim 28, wherein the at least one protrusion comprises sides and further comprising serrations on at least one side of the at least one protrusion.

32. The holder as defined in claim 28, wherein rotation of the sleeve couples the sleeve to the body.

33. The holder as defined in claim 28, wherein the sleeve comprises a view-port, and wherein the keyway and the projection are configured to limit rotation of the sleeve in the conduit so that the view port is positioned in a set orientation when the sleeve is rotated.

34. The holder as defined in claim 33 wherein the view-port faces a center of the disc space when rotation of the sleeve is inhibited by an end of the keyway contacting the protrusion.

35. The holder as defined in claim 28, further comprising a flange, the flange having an inner edge, an outer edge, a lower surface and an upper surface, wherein the flange is positionable around the body, and wherein the flange is configured to protect tissue and vessels adjacent to the disc space during use.

36. The holder as defined in claim 35, wherein the flange is made of a semi-rigid material.

37. The holder as defined in claim 35, wherein the lower surface of the flange curves during use to substantially match curvatures of surfaces of vertebrae adjacent to the holder.

38. The holder as defined in claim 35, further comprising a rim on a portion of an outer surface of the body, wherein the rim is configured to engage the lower surface of the flange to support the flange during use.

39. The holder as defined in claim 35, further comprising a groove on a portion of an outer surface of the body, wherein the groove is configured to engage the inner edge of the flange to support the flange during use.

40. The holder as defined in claim 35, wherein the flange further comprises an elastic collar configured to conform to the shape of the body during use to support the flange during use.

41. The holder as defined in claim 28, wherein a height of the body is less than about six inches.

42. The holder as defined in claim 28, wherein a height of the body is less than about four inches.

43. The holder as defined in claim 28, wherein a height of the body is less than about two inches.

44. The holder as defined in claim 28, further comprising at least one tang that couples the body to a first vertebra.

45. The holder as defined in claim 44, wherein the tang further comprises serrations on at least one side of the at least one tang.

46. The holder as defined in claim 28, further comprising a slot in a conduit wall, the slot configured to engage a distractor on an end of the sleeve during use.

47. The holder as defined in claim 28, wherein the sleeve further comprises a view-port to provide increased visibility of a surgical site during use.

48. The holder as defined in claim 28, wherein a bottom of the body is curved to substantially conform to curvatures of vertebrae adjacent to the holder during use.

49. The holder as defined in claim 28, further comprising a slot in the body and an insertion instrument, wherein the insertion instrument is configured to releasably engage the slot.

50. The holder as defined in claim 49 wherein the slot is an opening through the body.

51. The holder as defined in claim 28, further comprising a slot in the body and a removal instrument, wherein the removal instrument is configured to releasably engage the slot.

52. The holder as defined in claim 28, further comprising at least one tang, wherein the at least one tang is configured to engage the first vertebra to couple the body to the vertebra.

53. The holder as defined in claim 28, wherein the conduit comprises a non-circular perimeter, and wherein the conduit is configured to guide a non-cylindrical implant into the disc space.

54. A base for use during a spinal fusion procedure, comprising:
 a body;
 a tang extending from the body, the tang configured to couple the body to a first vertebra of a pair of vertebrae;
 a conduit through the body, wherein the conduit is configured to allow tools or devices for implanting a spinal fusion device, or for preparing a patient to receive a spinal fusion device, to be inserted into a disc space between the vertebrae;
 a sleeve, wherein an end of the sleeve is removably positionable in the conduit; and
 a slot in a conduit wall, the slot configured to engage a distractor on an end of the sleeve during use.

55. The base as defined in claim 54, wherein the tang further comprises surface roughening on at least one side of the tang.

56. The base as defined in claim 55, wherein the surface roughening comprises serrations.

57. The base as defined in claim 54, further comprising a shoulder in the conduit, the shoulder configured to limit insertion depth of the sleeve into the conduit.

58. The base as defined in claim 54, wherein the sleeve further comprises a view-port to provide increased visibility of a surgical site during use.

59. The base as defined in claim 54, further comprising a projection extending from a wall of the conduit, the projection configured to engage a slot in the sleeve.

60. The base as defined in claim 54, further comprising a protrusion extending from the body, the protrusion configured to be positionable within the disc space during use.

61. The base as defined in claim 60, wherein the protrusion establishes a separation distance between the first vertebra and the second vertebra during use.

62. The base as defined in claim 60, wherein the protrusion comprises sides and further comprising surface roughening on at least one side of the protrusion.

63. The base as defined in claim 62, wherein the surface roughening comprises serrations.

64. The base as defined in claim 54, further comprising an insertion tool, wherein the insertion tool is configured to releasably couple to a slot in a wall of the body.

65. The base as defined in claim 54, further comprising a flange, the flange having an inner edge, an outer edge, a lower surface and an upper surface, wherein the flange is positionable around the body, and wherein the flange is configured to protect tissue and vessels adjacent to the disc space during use.

66. The base as defined in claim 65, wherein the flange is made of a semi-rigid material.

67. The base as defined in claim 65, wherein the lower surface of the flange curves during use to substantially match curvatures of vertebrae adjacent to the base.

68. The base as defined in claim 65, further comprising a rim on a portion of an outer surface of the body, wherein the rim engages the lower surface of the flange to support the flange during use.

69. The base as defined in claim 65, further comprising a groove on a portion of an outer surface of the body, wherein the groove engages the inner edge of the flange to support the flange during use.

70. The base as defined in claim 65, wherein the flange further comprises an elastic collar which conforms to the shape of the body during use to support and secure the flange against the body.

71. The base as defined in claim 54, wherein a height of the body is less than about 15 centimeters.

72. The base as defined in claim 54, wherein a height of the body is less than about 10 centimeters.

73. The base as defined in claim 54, wherein a height of the body is less than about five centimeters.

74. The base as defined in claim 54, wherein the bottom of the body is curved to substantially conform to curvatures of vertebrae adjacent to the base during use.

75. The base as defined in claim 54, wherein the conduit comprises a non-circular perimeter, and wherein the conduit is configured to guide a non-cylindrical implant into the disc space.

76. A base for use during a spinal fusion procedure, comprising:
 a body;
 a first conduit through the body;
 a second conduit through the body; and
 a tang extending from the body, the tang configured to couple the body to a first vertebra during use;

a sleeve, wherein an end of the sleeve is removably positionable in the first conduit or the second conduit during use;

a slot on an inner surface of the first conduit, wherein the slot is configured to engage a distractor on an end of the sleeve during use; and wherein tools or devices inserted into the first conduit or the second conduit during use are positionable in a disc space adjacent to the first vertebra.

77. The base as defined in claim 76, wherein the sleeve further comprises a view-port to provide increased visibility of a surgical site during use.

78. The base as defined in claim 76, further comprising a projection extending from the body into the first conduit, wherein the projection is configured to engage a slot within the sleeve.

79. The base as defined in claim 76, wherein the sleeve further comprises a groove to engage a pin in the wall of the conduit during use.

80. The base as defined in claim 76, further comprising a shoulder in the first conduit, wherein the shoulder limits insertion depth of the sleeve into the first conduit.

81. The base as defined in claim 76, wherein the bottom of the body is curved to substantially conform to curvatures of vertebrae adjacent to the base during use.

82. The base as defined in claim 76, further comprising an aperture located on the top portion of the base, wherein the aperture is configured to engage the insertion tool in the base.

83. The base as defined in claim 76, further comprising a flange, wherein the flange is positionable around the body, and wherein the flange is configured to protect tissue and vessels adjacent to the disc space during use.

84. The base as defined in claim 83, wherein the flange is made of a semi-rigid material.

85. The base as defined in claim 83, wherein a lower surface of the flange curves during use to substantially match curvatures of surfaces of vertebrae adjacent to the body.

86. The base as defined in claim 83, wherein the flange further comprises an elastic collar configured to conform to the shape of the body to support the flange.

87. The base as defined in claim 83, further comprising a rim on a portion of an outer surface of the body, wherein the rim is configured to engage the lower surface of the flange during use.

88. The base as defined in claim 83, further comprising a groove on a portion of an outer surface of the body, wherein the groove is configured to engage the inner edge of the flange during use.

89. The base as defined in claim 76, wherein the first and second conduits are substantially parallel.

90. The base as defined in claim 76, wherein the conduits are angled relative to each other.

91. The base as defined in claim 90, wherein a distance between a centerline of the first conduit and a centerline of the second conduit at a top of the body is greater than a distance between centerlines of the conduits at the bottom of the body.

92. The base as defined in claim 91, wherein an angle between the centerlines of the conduits is less than about 30 degrees.

93. The base as defined in claim 91, wherein an angle between the centerlines of the conduits is less than about 20 degrees.

94. The base as defined in claim 91, wherein an angle between the centerlines of the conduits is between about 2 degrees and about 10 degrees.

95. The base as defined in claim 91, wherein the body further comprises two sides, and wherein the sides flare such that a largest width of the body measured from side to side is proximate the bottom of the body.

96. The base as defined in claim 76, wherein the first hole and the second hole are obliquely angled through the body relative to a vertical axis of the body.

97. The base as defined in claim 76, wherein a height of the body is less than about 15 centimeters.

98. The base as defined in claim 76, wherein a height of the body is less than about 10 centimeters.

99. The base as defined in claim 76, wherein a height of the body is less than about five centimeters.

100. The base as defined in claim 76, wherein a portion of the first conduit overlaps a portion of the second conduit.

101. A base for use during a spinal fusion procedure, comprising:

a body;

a tang extending from the body, the tang configured to couple the body to a first vertebra of a pair of vertebrae;

a conduit through the body, wherein the conduit is configured to allow tools or devices for implanting a spinal fusion device, or for preparing a patient to receive a spinal fusion device, to be inserted into a disc space between the vertebrae; and a flange, the flange comprising an inner edge, an outer edge, a lower surface and an upper surface, wherein the flange is positionable around the body, and wherein the flange is configured to protect tissue and vessels adjacent to the disc space during use.

102. The base as defined in claim 101, wherein the lower surface of the flange curves during use to substantially match curvatures of vertebrae adjacent to the base.

103. The base as defined in claim 101, wherein the flange further comprises an elastic collar which conforms to the shape of the body during use to support and secure the flange against the body.

104. A base for use during a spinal fusion procedure, comprising:

a body;

a first conduit through the body;

a second conduit through the body;

a tang extending from the body, the tang configured to couple the body to a first vertebra during use;

a sleeve, wherein an end of the sleeve is removably positionable in the first conduit or the second conduit during use;

a projection extending from the body into the first conduit, wherein the projection is configured to engage a slot within the sleeve; and wherein tools or devices inserted into the first conduit or the second conduit during use are positionable in a disc space adjacent to the first vertebra.

105. A base for use during a spinal fusion procedure, comprising:

a body;

a first conduit through the body;

a second conduit through the body; and a tang extending from the body, the tang configured to couple the body to a first vertebra during use;

a flange, wherein the flange is positionable around the body, and wherein the flange is configured to protect tissue and vessels adjacent to the disc space during use; and wherein tools or devices inserted into the first conduit or the second conduit during use are positionable in a disc space adjacent to the first vertebra.

106. The base as defined in claim 105, further comprising a rim on a portion of an outer surface of the body, wherein the rim is configured to engage the lower surface of the flange during use.

107. The base as defined in claim 105, further comprising a groove on a portion of an outer surface of the body, wherein the groove is configured to engage the inner edge of the flange during use.

108. A method of inserting an implant during a spinal fusion procedure, comprising:

inserting a holder in a disc space between a first vertebra and a second vertebra, wherein a portion of the disc space is beneath a first conduit, and wherein the first conduit extends through the holder from a top to a bottom of the holder;

securing the holder to the first vertebra and the second vertebra;

placing a sleeve into the first conduit of the holder;

rotating the sleeve to secure the first conduit of the holder;

preparing the disc space beneath the first conduit to receive a first implant with instruments inserted through the sleeve and through the first conduit; and inserting an implant into the disc space through the first conduit.

109. The method as defined in claim 108, further comprising:

removing the sleeve from the first conduit of the holder;

placing a sleeve in a second conduit of the holder, the second conduit extending through the holder from the top to the bottom;

preparing the disc space beneath the second conduit to receive an implant with instruments inserted into the disc space through the sleeve and holder; and inserting a second implant into the disc space through second conduit.

110. The method defined in claim 109, further comprising rotating the sleeve in the second conduit to secure the sleeve to the holder.

111. The method as defined in claim 108, further comprising placing a flange about an outer surface of the holder after the holder is inserted into the disc space to shield surrounding tissue and vessels during use.

112. The method as defined in claim 108, wherein the holder comprises at least one distractor, and wherein inserting the holder in a disc space comprises coupling a first end of a holder insertion device to the holder and hammering on a second end of the holder insertion device to drive the distractor into the disc space between the second vertebra and the first vertebra.

113. The method as defined in claim 108, further comprising driving a tang of the holder into a vertebra.

114. The method as defined in claim 113, wherein the holder comprises a distractor extending from the bottom and positionable between the vertebrae to maintain a separation distance between the vertebrae.

* * * * *